United States Patent [19]
Piontek et al.

[11] Patent Number: 5,617,626
[45] Date of Patent: Apr. 8, 1997

[54] METHOD OF TELESCOPICALLY ASSEMBLING A FLEXIBLE PINCH VALVE ELEMENT WITH A LENGTH OF FLEXIBLE TUBING

[76] Inventors: Carl J. Piontek, 118 Beech Ridge Dr., Powell, Ohio 43065; Bradford L. Buck, 3710 Peak Ridge Dr., Gahanna, Ohio 43230

[21] Appl. No.: 531,674

[22] Filed: Sep. 21, 1995

[51] Int. Cl.$^6$ ................................... B23P 11/02
[52] U.S. Cl. ................... 29/450; 251/4; 137/15
[58] Field of Search ................ 29/450, 234, 235, 29/754, 881; 251/4; 137/15

[56] References Cited

U.S. PATENT DOCUMENTS

| | | | |
|---|---|---|---|
| 1,037,159 | 8/1912 | Lorenz | 29/235 |
| 2,574,195 | 11/1951 | Sherrick | 29/235 |
| 2,683,924 | 7/1954 | Schryver | 29/754 |
| 2,922,613 | 1/1960 | Beacham et al. | 251/4 |
| 3,138,946 | 6/1964 | Amthor, Jr. et al. | 251/4 |
| 4,063,706 | 12/1977 | Osborne, Sr. | 29/451 |

FOREIGN PATENT DOCUMENTS

| | | | |
|---|---|---|---|
| 103277 | 2/1924 | Switzerland | 251/4 |
| 939324 | 10/1963 | United Kingdom | 251/4 |
| 2037935 | 7/1980 | United Kingdom | 29/450 |

*Primary Examiner*—David P. Bryant
*Attorney, Agent, or Firm*—Brian R. Woodworth

[57] ABSTRACT

A method of assembling telescopically a flexible tubular segment with a length of tubing involves the use of an assembly apparatus which controllably stretches a tubular segment. The free end of a portion of an end of a length of tubing is inserted through the stretched tubular segment a preselected distance. The stretched tubular segment is allowed to relax around the inserted portion of an end of the length of tubing, thus assembling the tubular segment with the end portion of a length of tubing. The tubular segment and portion of an end of a length of tubing that have been assembled together are then ejected simultaneously from the assembly apparatus.

3 Claims, 23 Drawing Sheets

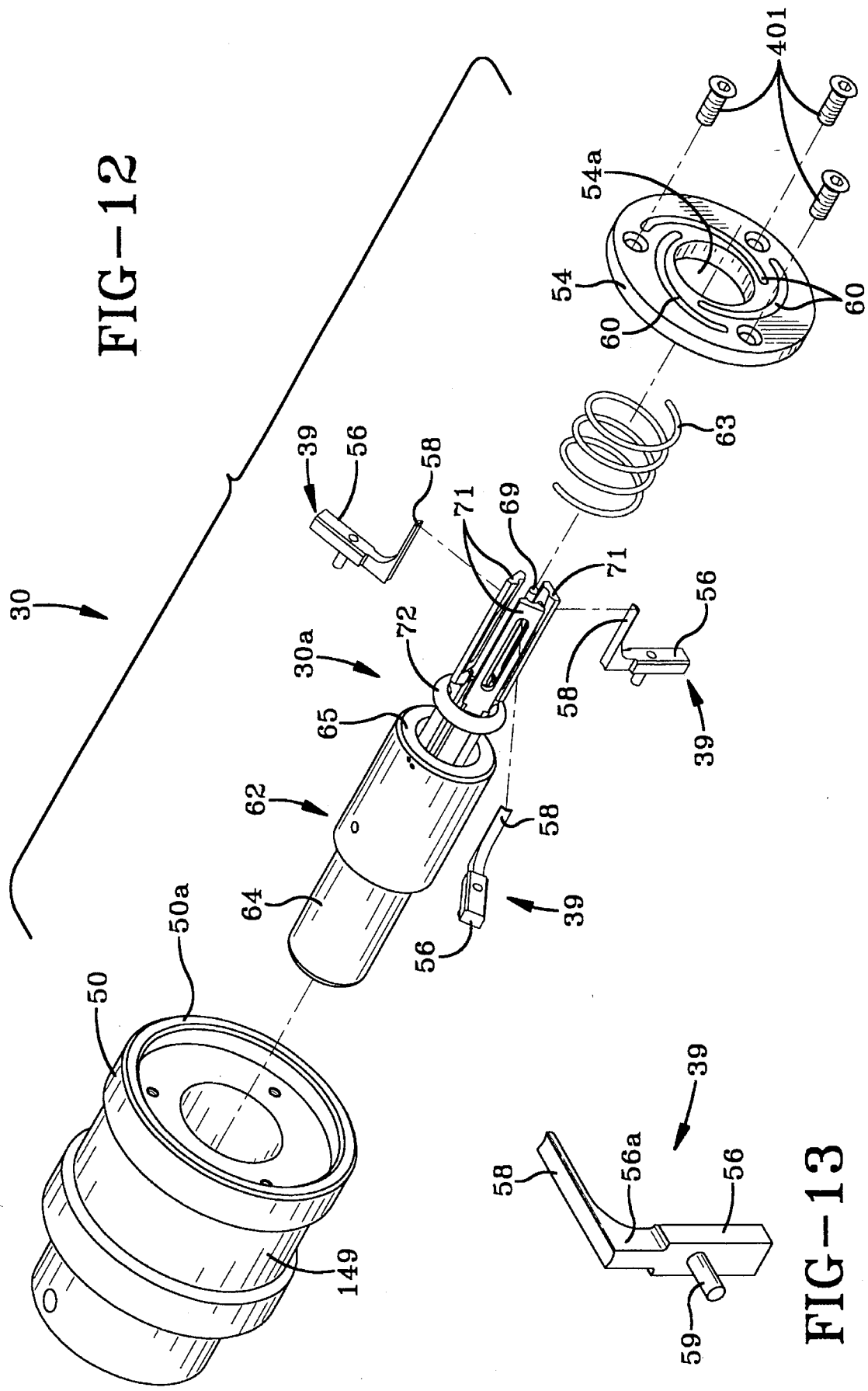

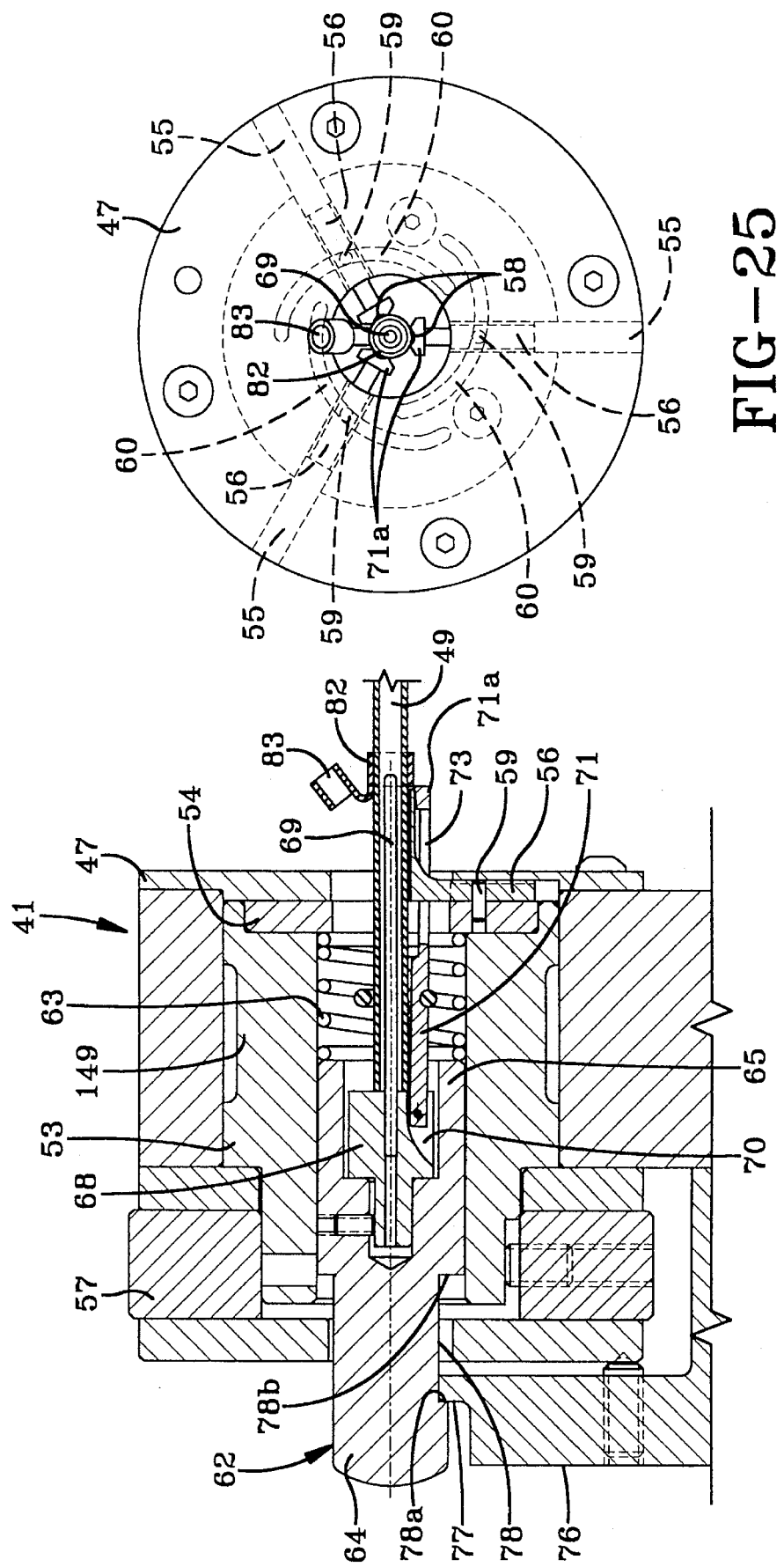

METHOD OF TELESCOPICALLY ASSEMBLING A FLEXIBLE PINCH VALVE ELEMENT WITH A LENGTH OF FLEXIBLE TUBING

FIELD OF THE INVENTION

The invention relates to a method for assembling one or more elastic foreshortened tubular segments telescopically upon and near an end of a tube or length of tubing having an outer diameter at least as great as the inner diameter of the tubular segment.

BACKGROUND OF THE INVENTION

In the manual assembly of tubing lengths or pieces together or to a vessel of some sort, connection is usually made by use of a rigid or somewhat rigid tubular connector element or connector portion in the form of a male element with a female element, the male element having a slightly smaller outer diameter than the inner diameter of the female element, with retention assured by adhesive bonding.

However, accurate assembly of a very short tubular segment of flexible elastic tubing, telescopically, upon a length of tubing having an outer diameter substantially the same or greater than the inner diameter of the tubular segment, and at a predetermined distance away from an end of the length of tubing, is difficult to do manually, and it is believed no device or apparatus therefor existed prior to the development of the apparatus of the present invention. The assembly has been especially difficult, heretofore, if a very short flexible tubular segment was to be assembled telescopically upon a length of tubing that is flexible as well as having an outer diameter substantially the same or greater than the inner diameter of the tubular segment.

A chuck is commonly used to hold a work piece in a lathe or a drill bit in a drill motor. However it is not believed that any use has been made heretofore of chuck-like jaws as spreaders or stretching elements instead of as compressive grasping elements.

SUMMARY OF THE INVENTION

There is provided in accordance with the present invention a method of assembling telescopically a flexible tubular segment with a length of tubing comprising the following sequence of steps: providing an assembly apparatus including: means for controllably radially stretching a tubular segment during insertion of a portion of an end of the length of tubing and controllably allowing the tubular segment to radially relax thereafter; means for limiting the depth of insertion of the portion of the end of the length of tubing to a preselected depth; and means for ejecting, from the means for radial stretching and relaxing, a tubular segment and end portion of a length of tubing that have been telescopically assembled together; radially stretching the tubular segment using said means therefor; inserting the free end of a portion of an end of the length of tubing through the radially stretched tubular segment to the preselected depth; allowing the stretched tubular segment to relax around the inserted portion of an end of the length of tubing, thus assembling the tubular segment with the end portion of a length of tubing; and ejecting simultaneously the tubular segment and portion of an end of a length of tubing that have been assembled together.

There is provided in accordance with another aspect of the invention a method of assembling telescopically a flexible pinch valve element with a length of flexible tubing to form a flexible, tension responsive, pinch valve, the pinch valve element having first and second tubular segment end portions joined by a shank portion and the length of flexible tubing having an outer diameter substantially the same or greater than the diameter of the tubular segments, comprising the following sequence of steps: providing a first assembly apparatus including: means for controllably radially stretching a tubular segment end portion of a pinch valve element during insertion of a portion of an end of the length of flexible tubing and controllably allowing the tubular segment end portion to radially relax thereafter; means for limiting the depth of insertion of the portion of the end of the length of flexible tubing to a first preselected depth; and means for ejecting, from the means for radial stretching and relaxing, a tubular segment end portion and length of flexible tubing that have been telescopically assembled together; radially stretching the first tubular segment end portion using said means therefor; inserting the portion of an end of the length of flexible tubing through the radially stretched first tubular segment end portion to the first preselected depth; allowing the stretched first tubular end portion to relax around the inserted portion of an end of the length of flexible tubing, thus assembling the first tubular segment end portion with the length of flexible tubing; ejecting simultaneously the first tubular segment end portion and portion of an end of a length of flexible tubing that have been assembled together; providing a second assembly apparatus including: means for controllably radially stretching a tubular segment end portion of a pinch valve element during insertion of a portion of an end of the length of flexible tubing and controllably allowing the tubular segment end portion to radially relax thereafter; means for limiting the depth of insertion of the portion of an end of the length of flexible tubing to a second preselected depth; and means for ejecting, from the means for radial stretching and relaxing, a tubular segment end portion and portion of an end of a length of flexible tubing that have been telescopically assembled together; advancing to the means for spreading of the second assembly apparatus and placing thereon the second tubular segment end portion that is attached by said shank portion to the first tubular segment end portion that has been assembled with the length of flexible tubing; radially stretching the second tubular segment end portion using said means therefor; doubling over the portion of the end of the length of flexible tubing upon which the first tubular segment end portion has been assembled and inserting the free end thereof through the radially stretched second tubular segment end portion to a second preselected depth, the second preselected depth being shallower than the first preselected depth by a differential length substantially greater than the length of said shank portion; allowing the stretched second tubular segment end portion to relax around the inserted portion of the free end of the portion of an end of the length of flexible tubing on which the first tubular segment end portion has been assembled, assembling the second tubular segment end portion with the portion of an end of the length of flexible tubing; and ejecting simultaneously the second tubular segment end portion and portion of an end of a length of flexible tubing that have been assembled together.

BRIEF DESCRIPTION OF THE DRAWINGS

FIG. 12 is an enlarged exploded perspective view of all the components of the subassembly identified by reference character 30 in FIG. 8 with the components shown in FIG. 11 already assembled together;

FIG. 13 is a greatly enlarged perspective view of an "L"-shaped spreader finger element showing the guide pin extending laterally from the leg portion;

FIG. 24 is a fragmentary view in section of the assembly apparatus with the tubular segment of the pinch valve relaxed upon the length of tubing and with the ejector piston moved forward;

FIG. 25 is a front elevation of the portion of the assembly apparatus encompassed by the cover plate at the point of the assembly process illustrated in FIG. 24;

DETAILED DESCRIPTION OF THE INVENTION

Figure 1:
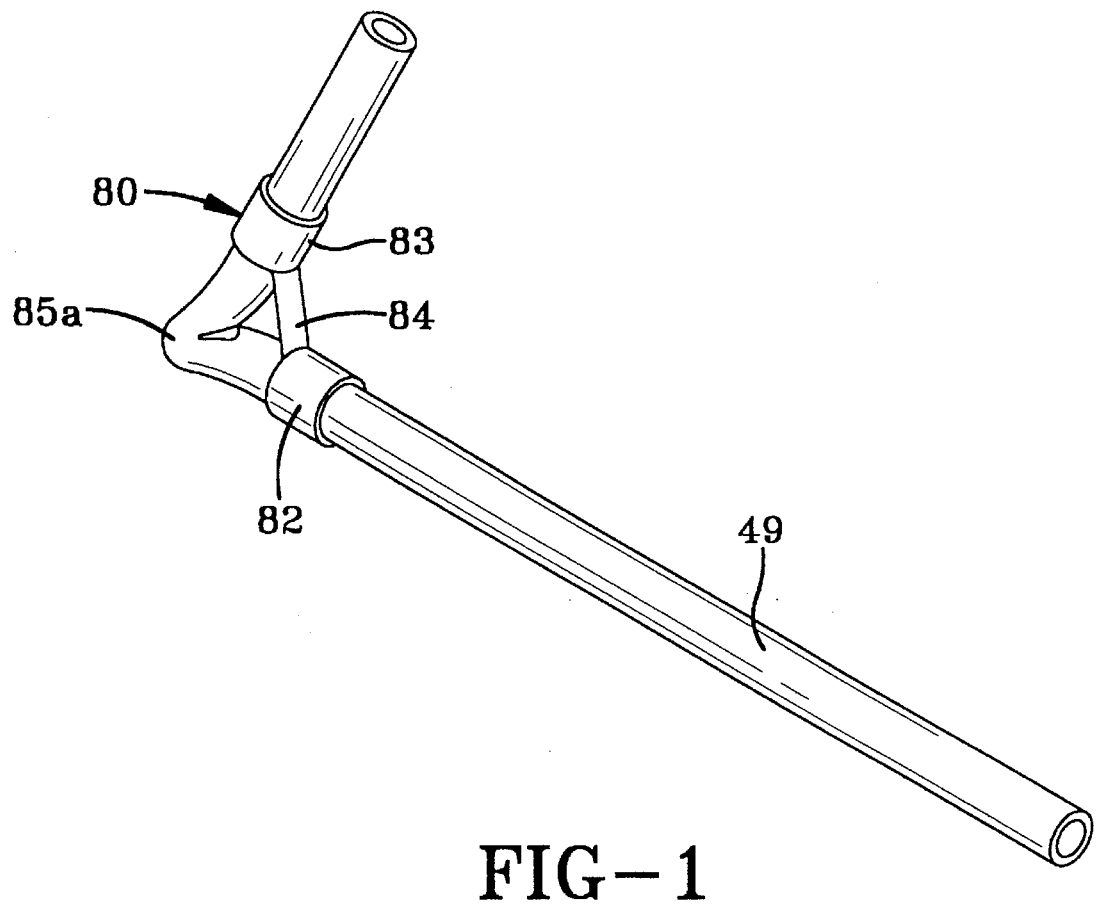
FIG. 1 is a perspective view of a device having flexible tubular segments emplaced upon a length of tubing and assembled using the apparatus of the invention.

The assembly apparatus of the invention has utility for placing a flexible, and at least somewhat elastic, foreshortened tubular segment telescopically upon and near an end of a length of tubing having an outer diameter substantially the same or greater than the inner diameter of the tubular segment. For example, a tension responsive pinch valve, such as that shown in FIG. 1, may be made by telescopically assembling a flexible pinch valve element 80 with a length of flexible tubing 49. The flexible pinch valve element has two end portions 82,83 in the form of tubular segments joined by a shank 84. The length of tubing has an outer diameter substantially the same or greater than the inner diameter of the tubular segments.

The term "tension responsive pinch valve" refers to a valve that opens when the flexible tubing, of which it is in part formed, is placed under tension, and closes when the tension is released.

Figure 2:
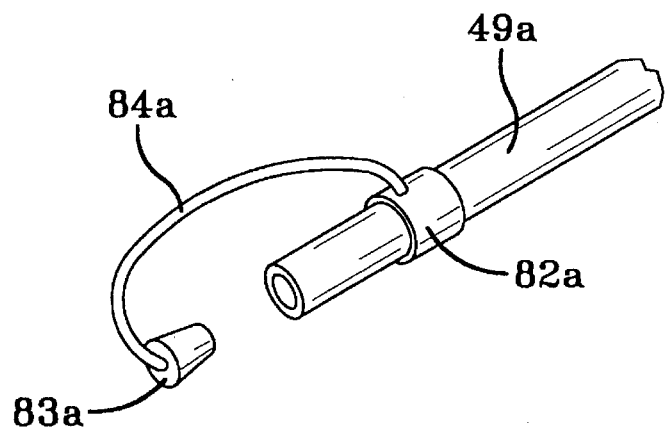
FIG. 2 is a perspective view of a second device having a flexible tubular segment emplaced upon a length of tubing and assembled using the apparatus of the invention.

FIG. 2 shows another assembly of a length of tubing 49a with a single flexible tubing segment 82a having an end cap or stopper 83a attached thereto by a tether 84a. Such a structure is useful when it is desired to have a reusable closure at the end of a supply or delivery tube.

A very important aspect of the assembly apparatus disclosed herein is the capacity to eject the assembled combination of a flexible tubular segment and a length of tubing from the assembly apparatus without displacing the flexible tubular segment longitudinally along the length of tubing.

For the purposes of the specification and claims it should be understood that the front side or surface, also referred to herein as a first surface, of the assembly apparatus is the side or surface into which the length of tubing is inserted for emplacement of a flexible tubular segment thereon, while the back or rear side or surface is opposite the front side or surface. A forward motion is a motion towards the front side or surface as here defined, while a rearward motion or extension is taken in the opposite direction.

Figure 3:
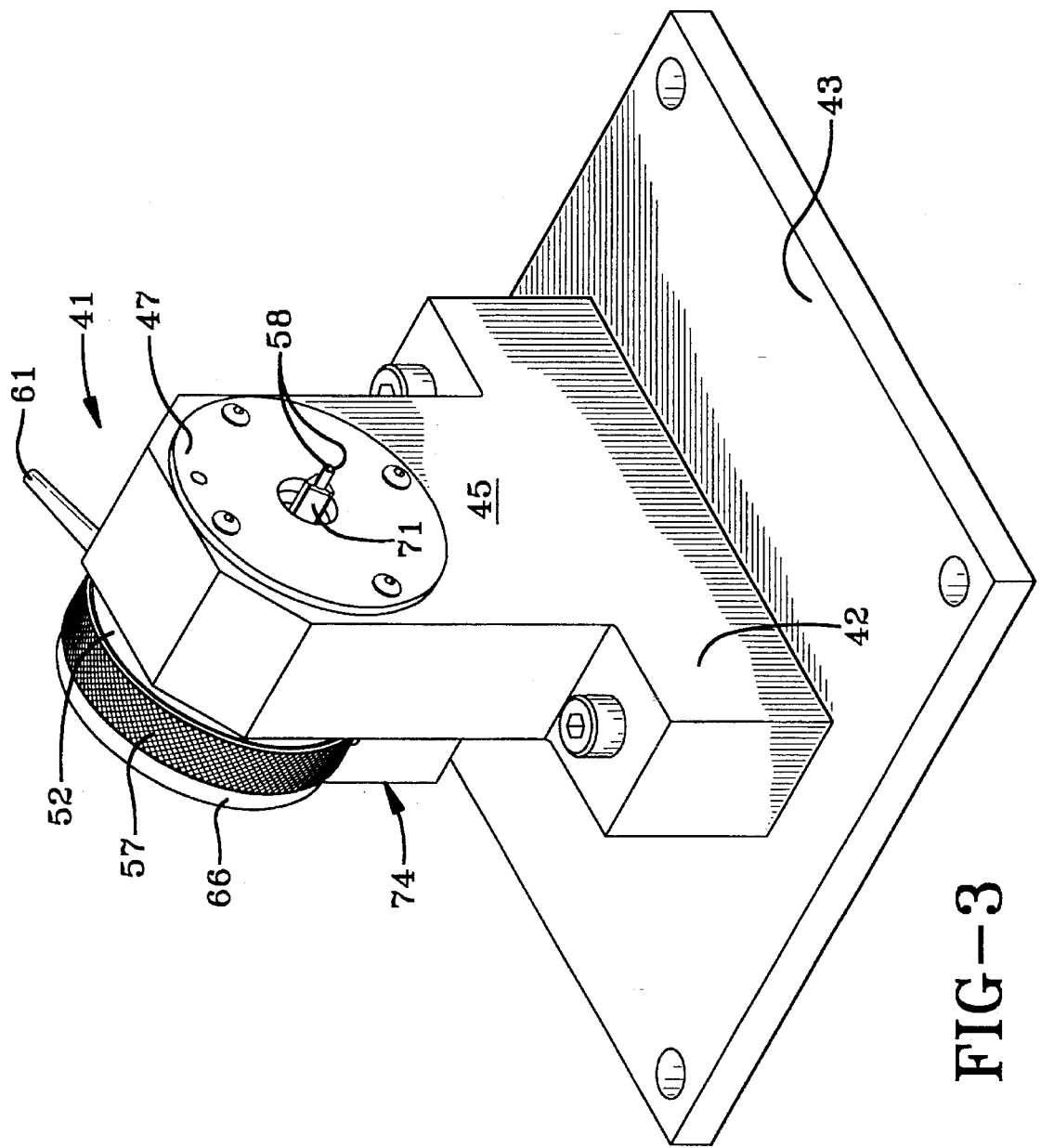
FIG. 3 is a perspective view of the front and side of an assembly apparatus of the invention.
Figure 4:
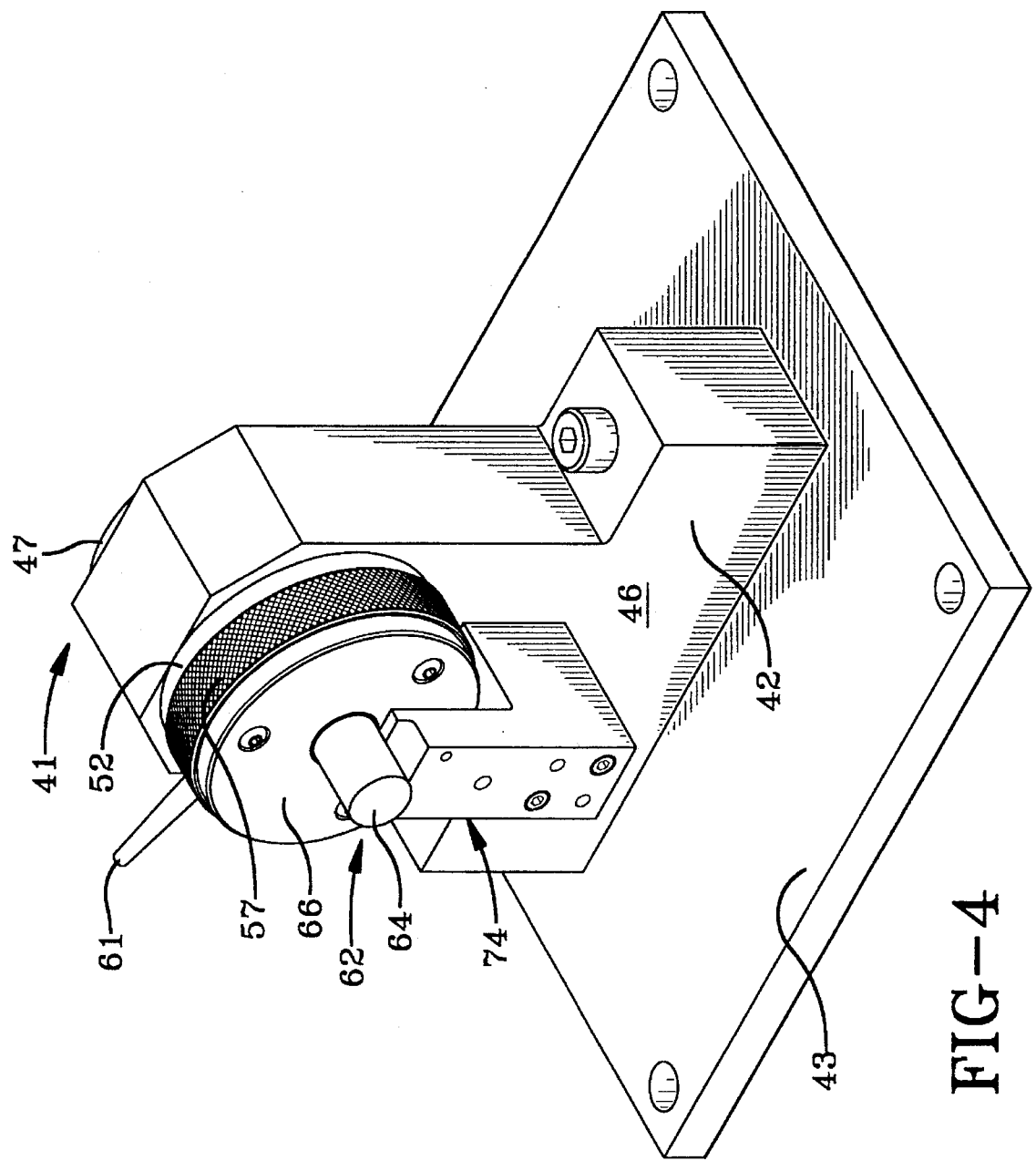
FIG. 4 is a perspective view of the back and side of the assembly apparatus of FIG. 1.
Figure 5:
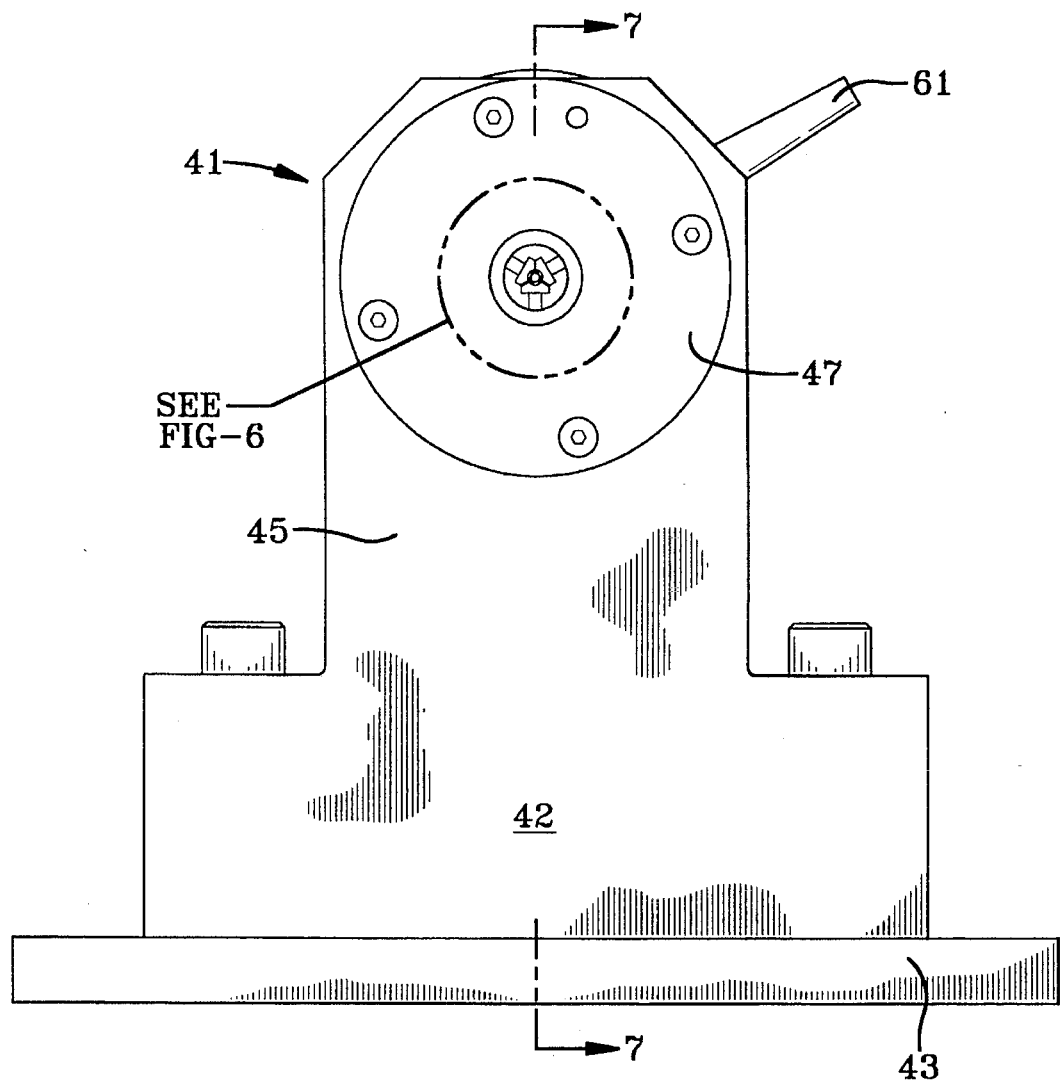
FIG. 5 is front elevation view of the assembly apparatus of FIG. 1.
Figure 6:
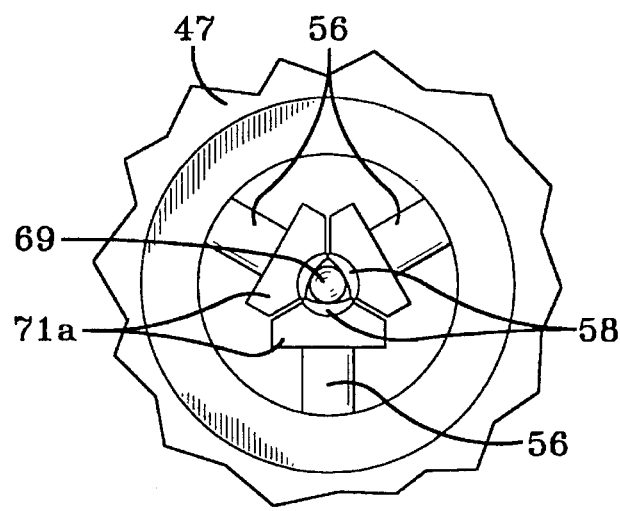
FIG. 6 is very greatly enlarged fragmentary view of the portion of FIG. 5 encircled by a dashed line.
Figure 7:
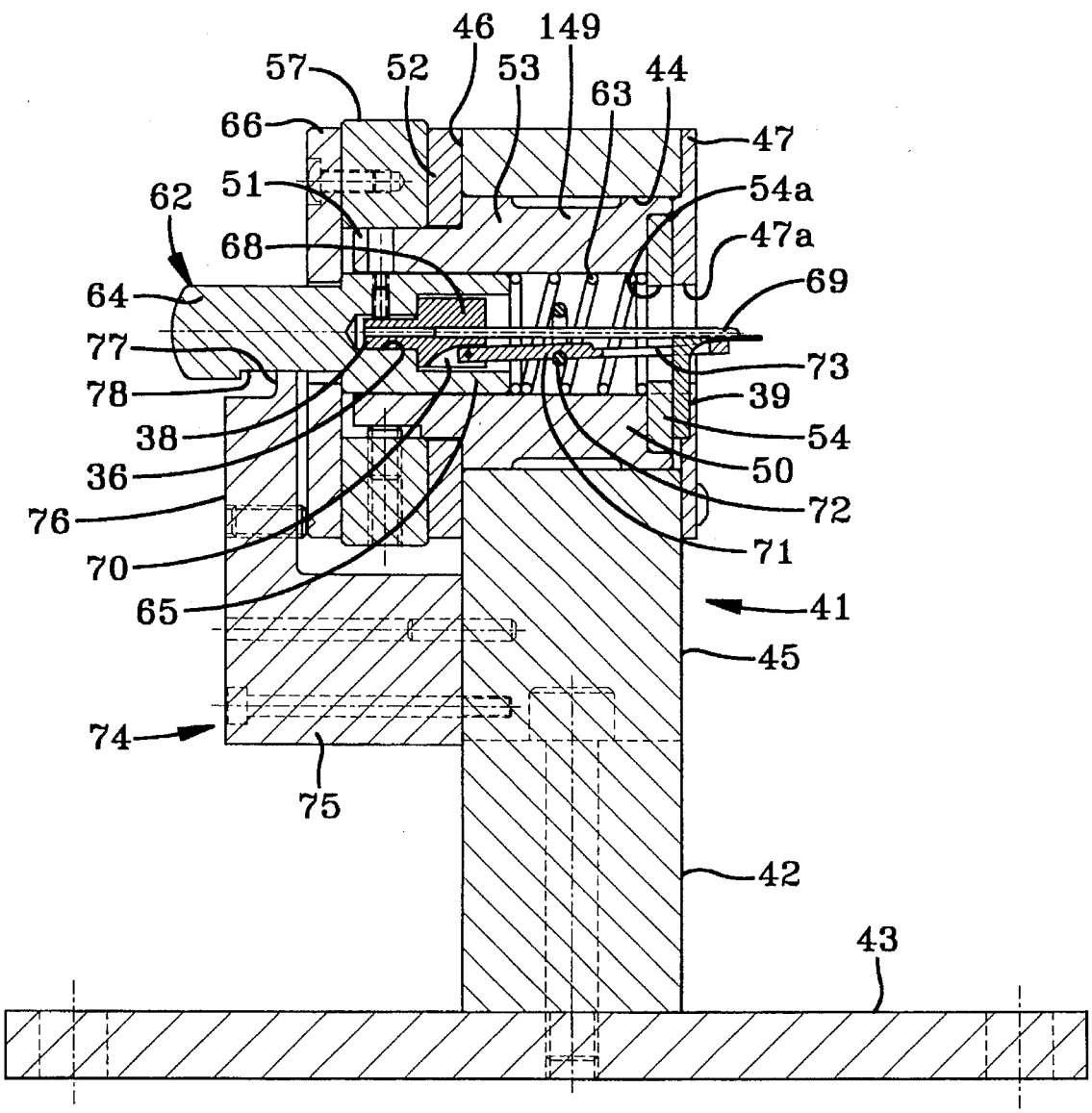
FIG. 7 is a view in vertical section of the assembly apparatus taken along the line 7—7 of FIG. 5.
Figure 8:
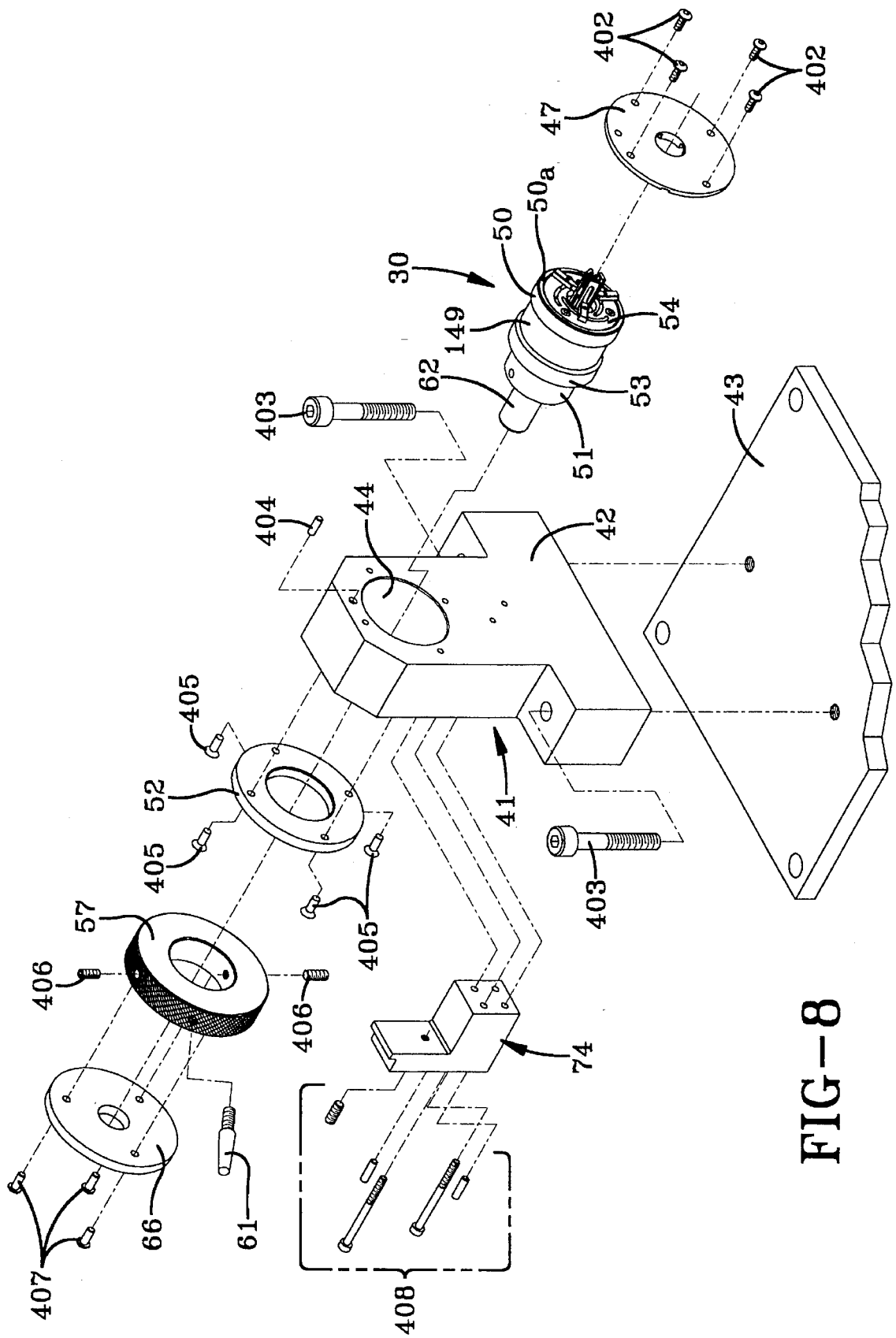
FIG. 8 is an exploded perspective view of the components of an assembly apparatus of the invention with a corner of the base plate cut away for purposes of illustration.

As seen in the exemplary embodiment shown in FIGS. 3-5, and the view in section in FIG. 7, along with the exploded view in FIG. 8, the present assembly apparatus is made up of a body portion, indicated generally by the reference numeral 41, which may if desired have a base support portion 42, which may be secured to a base plate 43, for example by bolts 403, if desired, for stability during use. It is to be understood that the support structure may take any suitable shape and orientation and the parts thereof attached together by any suitable means such as welding or clamping.

As seen in FIG. 8, the exemplary assembly apparatus consists mainly of the body portion and suitable base or support portions in addition to a sub-assembly indicated generally by the reference numeral 310, a cover plate 47, a first retainer ring 52, a control ring 57, a second retainer ring 66 and a rear support element 74. In the assembled apparatus the sub-assembly 30 having controllably spreadable and retractable spreader finger portions is positioned in a cylindrical bore 44 that extends through the body portion 41 from the first, or front, face to the second, or rear, face and the other components are attached in the sequence and positions indicated, using screws and bolts 402, 405, 406, 407, 408 or other suitable fastening means.

The combination of the sub-assembly 30 with spreader finger elements 39, as seen in exploded view in FIG. 12, together with the cover plate 47 and the control ring 57, when mounted in the body portion 41 comprises a mechanical means for assembling a tubular segment with a length of tubing. Moreover, an integral part of the sub-assembly positioned concentrically and reciprocably within the mechanical means for assembly constitutes means for ejecting an assembly of a tubular segment with a length of tubing as will be further described herein.

The means for assembly which includes mechanical means for spreading and retracting the spreader finger elements 39 is described in detail below and is comprised primarily of: (1) a substantially cylindrical rotatable sleeve 149, that is rotatable in the cylindrical bore 44 of the body portion 41 of the apparatus; (2) a control ring 57 for rotating the rotatable sleeve 149; (3) a disc-like member 54 having radially, i.e., spirally, extending spiral guideways 60 formed therethrough and being mounted co-axially upon a first end of the rotatable sleeve 149 in an annular recess; and (4) at least three spreader finger elements, indicated generally by the numeral 39, that are supported by a combination of the disc-like member 54 and the cover plate 47 and radially spread or retracted by co-action of the disc-like member and the cover plate with the spreader finger elements.

The ejector means comprise: (1) a reciprocable piston 62, depicted in FIGS. 11 and 12 as part of the assembly apparatus shown in differing stages of the assembly process; (2) an ejector block 68 or 68a as depicted in FIGS. 9 and 10; and (3) ejector arms 71, in addition to the rotatable sleeve 149 in the cylindrical passageway of which the piston 62 is reciprocable.

The subassembly identified by reference character 30 in FIGS. 8, 12, 14 and 15, then, includes the substantially cylindrical rotatable sleeve 149 with a cylindrical passageway extending therethrough and into which there is positioned co-axially the reciprocable piston, indicated generally by the numeral 62. The reciprocable piston has a recess in one end into which there is positioned co-axially an ejector block such as ejector block 68 or 68a depicted in FIGS. 9 and 10. The ejector block has a plurality, in this example three, longitudinal slots 70 therein and in which are pivotally mounted, using pins 71b, ejector arms 71 substantially parallel to the longitudinal axis of the piston 62, bearing in mind that when the assembly apparatus is fully assembled, the piston is co-axial with the bore 44 through the body portion 41.

Figure 9:
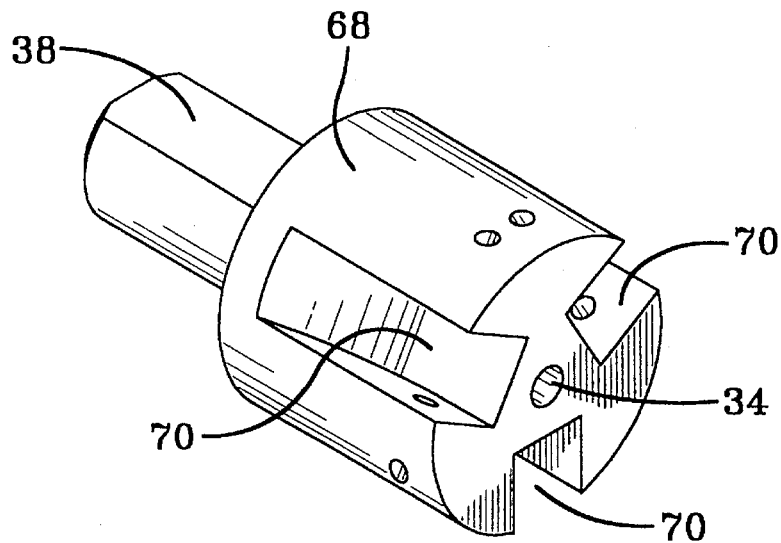
FIG. 9 is a greatly enlarged perspective view of an ejector block which may be used as a part of a sub-assembly identified by reference character 30 in FIG. 8.
Figure 10:
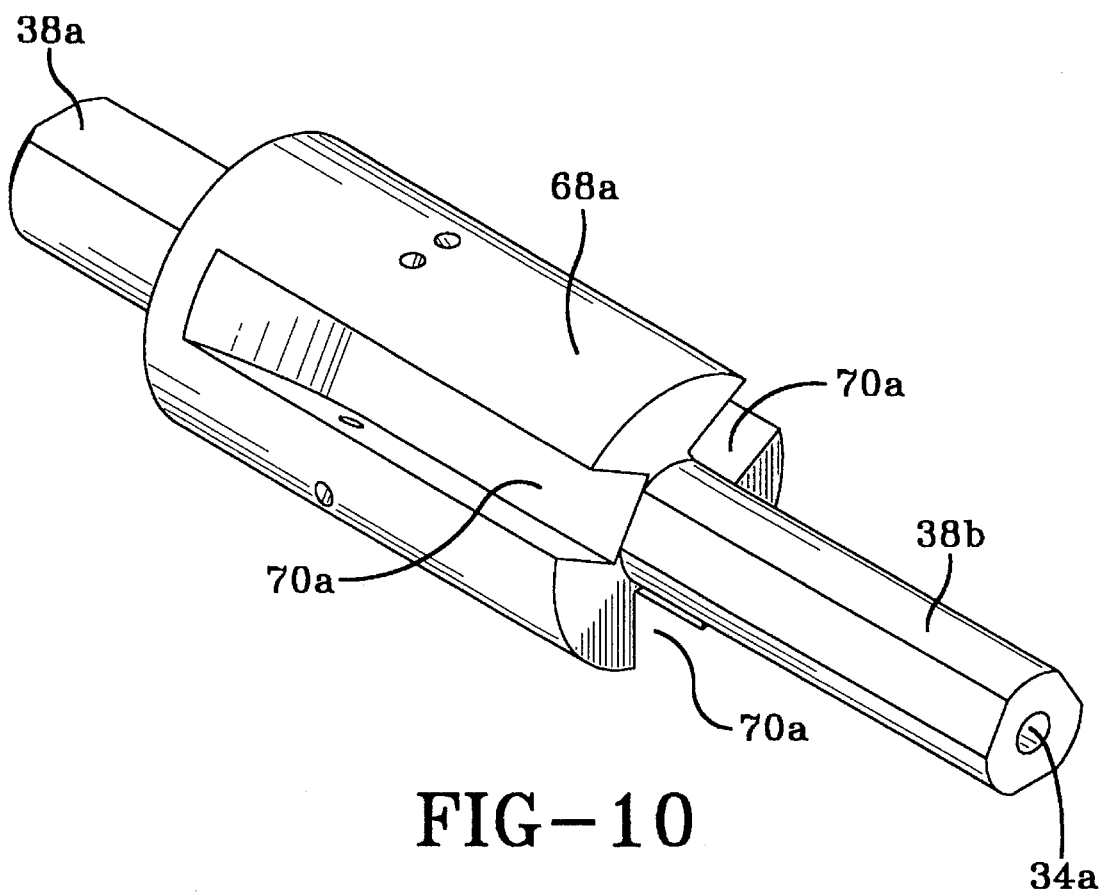
FIG. 10 is a greatly enlarged perspective view of another ejector block which may be used in a modification of the sub-assembly identified by reference character 30 in FIG. 8.

In a recess in the first end 65 of the piston 62 there is mounted in any suitable manner an ejector block 68, such as the ejector block shown in FIG. 9. The ejector block shown in FIG. 9 has a rearwardly extending tongue-like portion 38 that fits into a complementary borehole or passageway 36 in the piston 62 and is secured by a setscrew 37. The overall longitudinal length of the ejector block used in the assembly apparatus determines the distance from the end of the length of tubing where the tublar segment end portion will be emplaced during the assembly process.

In assembling a pinch valve element with two tubular segments as end portions it is necessary to assemble each tubular end portion with a given length of tubing in a separate operation in which an assembly apparatus is used with an ejector block having the appropriate length. Thus a shorter ejector block such as that shown in FIG. 9 would be used to emplace the first tubular segment, e.g. 82, while a longer ejector block 68a, as shown in FIG. 10, would be used in assembling the second tubular segment, e.g. 83, with the length of tubing to get the proper positioning of the tubular segments and achieving also the proper spacing longitudinally along the flexible tubing between the tubular segments. The ejector block 68a is provided with a forwardly projecting axial extension 38b that has a large enough cross-section to serve as a stop for the length of tubing, but is small enough to facilitate use of a coil spring 63 to make the piston 62 recoil after the ejection step.

In assembling the present apparatus the subassembly 30 seen in FIG. 8 is made up by selecting an ejector block 68 (or alternatively ejector block 68a of FIG. 10) of suitable dimensions, such as the ejector block depicted in FIG. 9, and positioning a plurality of pivotal ejector arms 71 in respective slots 70 formed in the sides of the ejector block 68 where the ejector arms are pivotally retained by pins 71b that pass through the walls of the slots and through the ejector arms near a first end 33 of each arm. The number of ejector arms 71 and complementary slots 70 employed is preferably at least three to match the number of spreader finger elements 39. The ejector arms 71 are oriented substantially parallel to the axis of the ejector piston 62. The rearward projecting tongue-like portion 38 of the ejector block 68 is inserted into the axial borehole 36 in the end 65 of the piston 62 and secured with a set screw as shown in FIG. 7.

Figure 11:
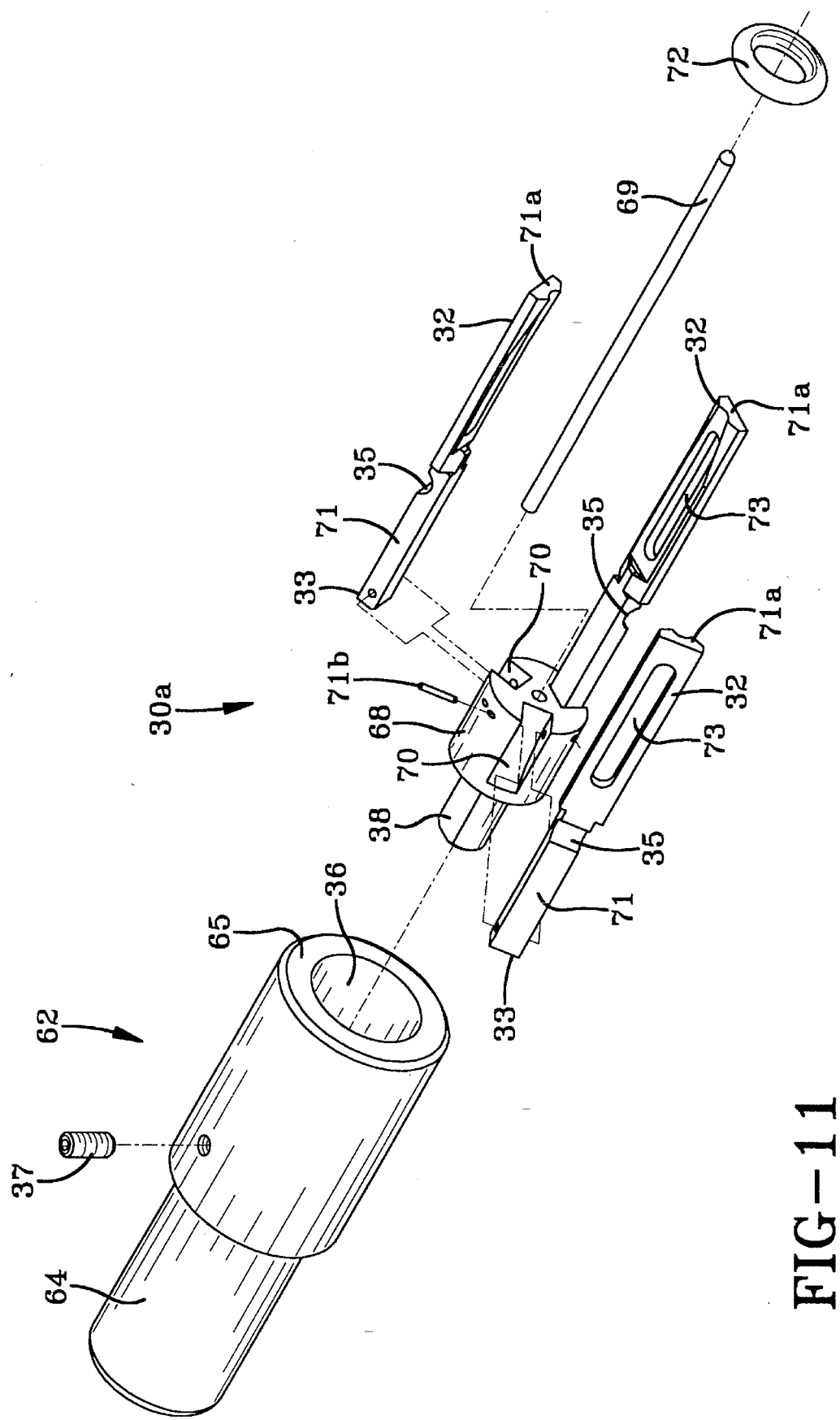
FIG. 11 is an enlarged exploded perspective view of some of the components of the subassembly identified by reference character 30 in FIG. 8, including the ejector block of FIG. 9.

Referring now to FIGS. 7 and 11, an elongated central guide rod 69 is inserted into and secured in any suitable manner in a longitudinal axial borehole 34 in the free end of the ejector block 68, or, in a longitudinal axial borehole 34a of the axial extension 38b of ejector block 68a if the longer extension block is part of the subassembly.

Turning again to FIGS. 11 and 12, an elastic annular member 72, which may be a conventional "O"-ring, is placed around the ejector arms 71 at about mid-length, for example at notches 35 in the arms, to retain them clustered together around the spreader finger portions 58 in the final assembly.

Figure 15:
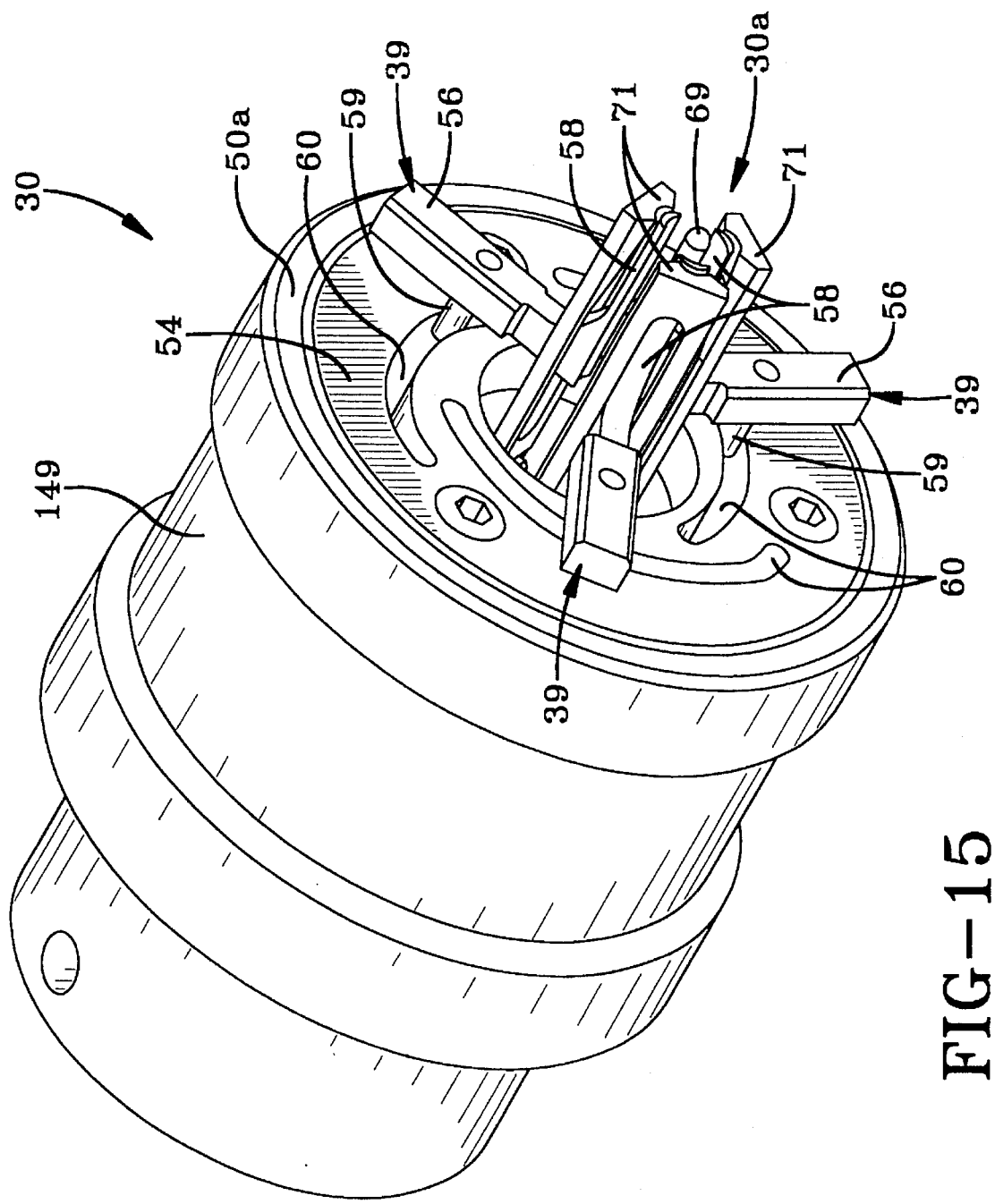
FIG. 15 is a very greatly enlarged perspective view of the sub-assembly identified by reference character 30 in FIG. 8.

Adjacent the second end 32 of each of the ejector arms 71 is an elongated longitudinally extending slot 73 formed therethrough. Through each of the slots 73 a respective leg portion 56 of a spreader finger element 39 extends radially outward from the line of the axis of the piston 62. As seen in FIGS. 12, 13 and 15, the spreader finger elements 39 are "L"-shaped, each with a leg portion 56 and a thin finger, i.e., finger portion, 58. To accommodate reciprocal movement of the ejector arms 71 along the axial line during an ejection step without interfering with the normal function of the spreader finger elements 39, the leg portion 56a that joins the finger portion 58 to the leg portion 56 in each element is preferably made thin enough so that the sides of the slot 73 do not bind against the leg portion 56a.

The means for assembling a tubular segment telescopically upon a length of tubing form part of the subassembly 30, which includes the spreader finger elements 39. The mechanical means for radially spreading the spreader finger portions include the disc-like member 54 as well as the rotatable sleeve 149 on which the disc-like member 54 is mounted. The cover plate 47 with its radial channels 55, while not part of the subassembly 30, is also an essential part of the mechanical means for spreading and retracting the spreader finger portions in cooperation with the disc-like member 54 and its spiral guideways 60.

As best seen in FIG. 13, each spreader finger element 39 is provided with a guide pin 59 that extends laterally from about mid-length of the leg portion 56 so as to extend into a spiral guideway 60 of the immediately adjacent disc-like member 54. With the spreader finger elements 39 restricted by the radial channels 55 of the cover plate 47 so that they cannot rotate, rotation of the disc-like member 54 provides cam-like action as the guide pins 59 are forced to slide along the respective spiral guideways 60, moving the spreader finger elements 39, and their finger portions 58, radially outward or inward, depending on the direction of rotation.

Figure 14:
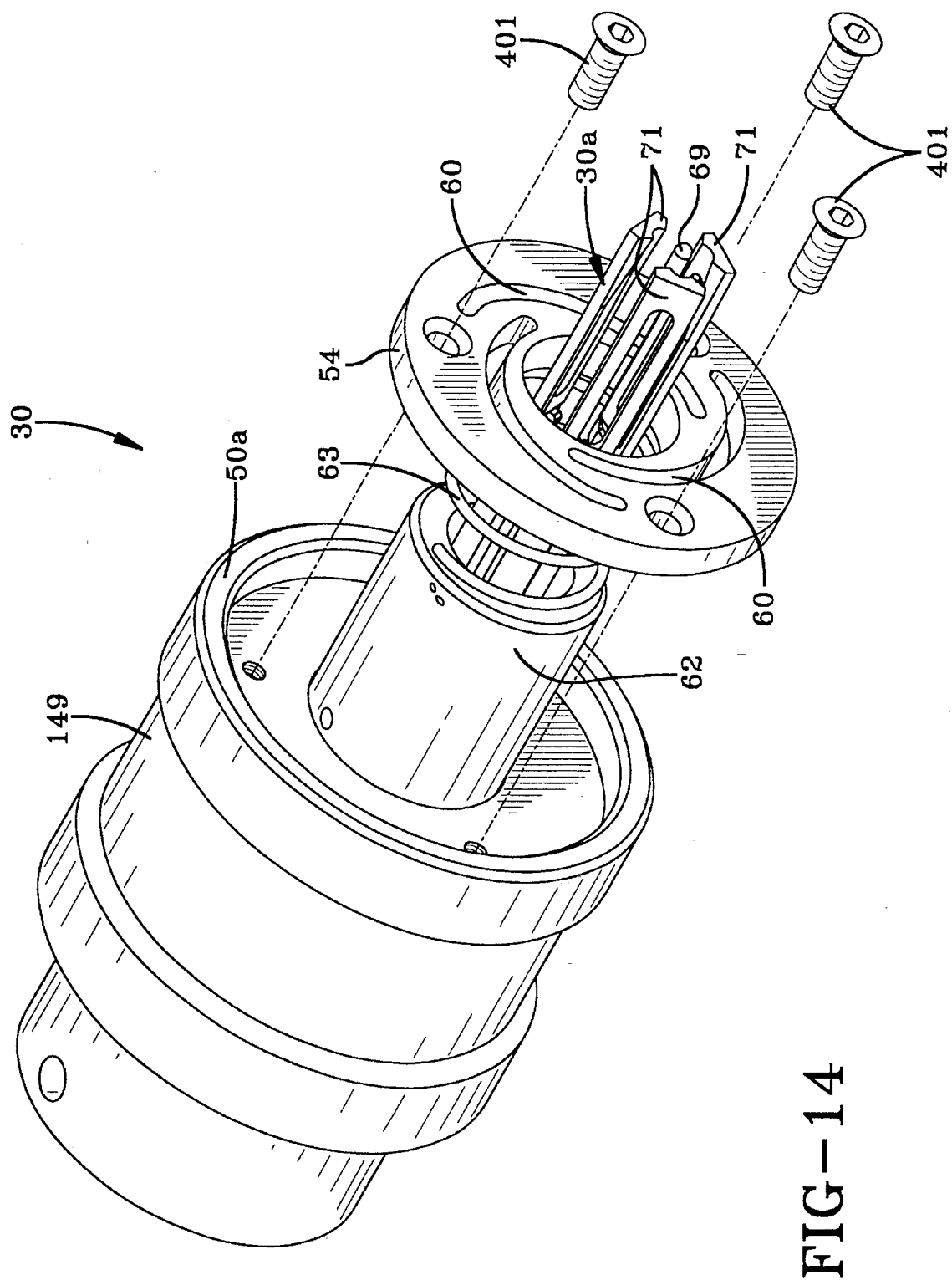
FIG. 14 is a very greatly enlarged partly exploded perspective view of the sub-assembly identified by reference character 30 in FIG. 8 in the process of being assembled.

In further assembling the subassembly 30 of FIG. 8, as seen in FIG. 14, a coil spring 63 is slid over the cluster of ejector arms 71, followed by the disc-like member 54 preparatory to attaching it as by threaded fasteners 401 to the annular end face of the rotatable sleeve 149, after sliding the piston 62 further into the passageway of the rotatable sleeve 149, as seen in FIG. 15. Also seen in FIG. 15 are the spreader finger elements 39 positioned with the finger portions 58 clustered concentrically inside the cluster of ejector arms 71 and around the central guide rod 69.

Figure 16:
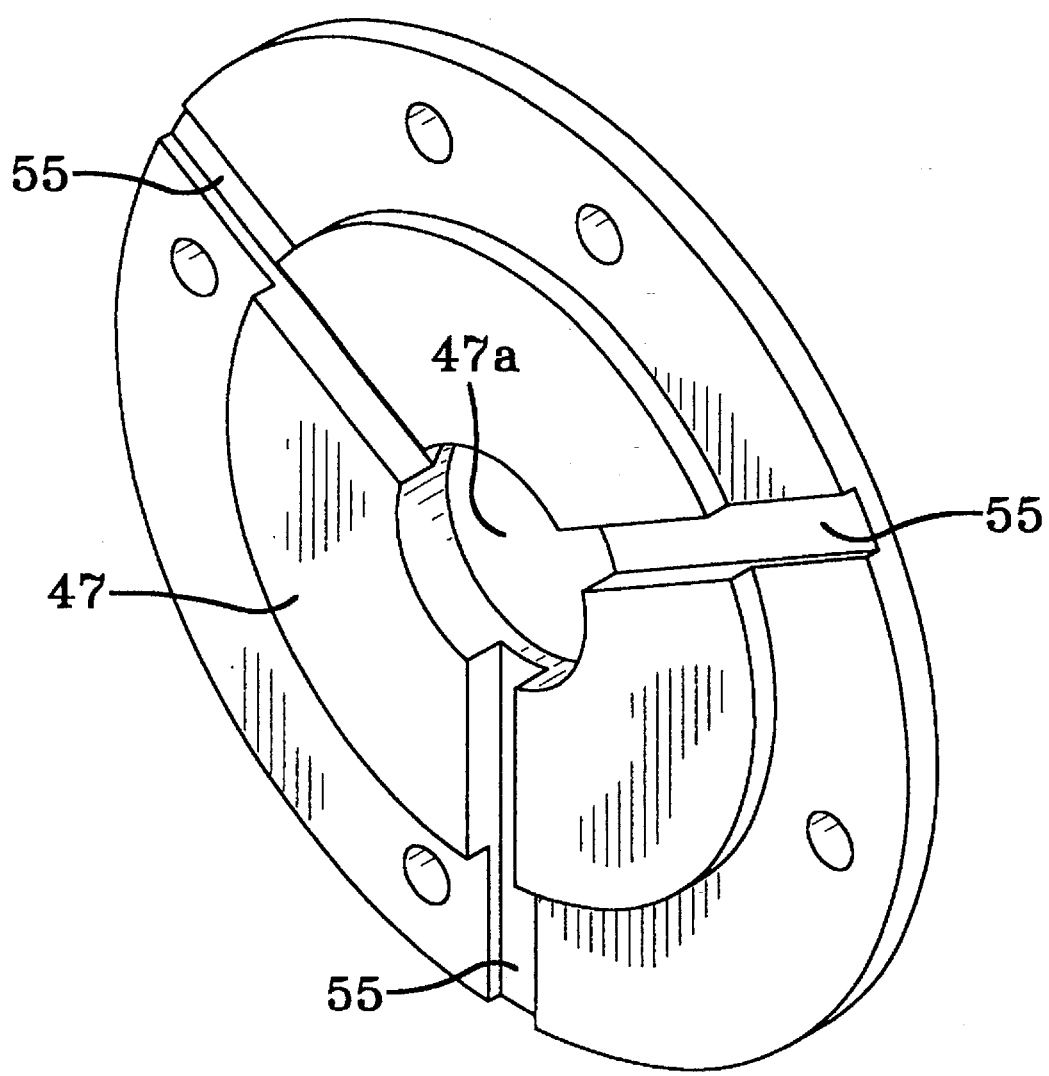
FIG. 16 is a perspective view of the reverse or inside face of the cover plate.

The subassembly 30 seen in FIG. 8 and largely contained within the rotatable sleeve 149 can now be inserted into the body portion 41 from the first or front side 45 thereof into the bore 44 and partially extending beyond the second or rear side 46 of the body portion 41 and positioned as seen in FIG. 7, so that the cover plate 47 can be attached by threaded fasteners 402, preferably using a locator pin 404 to align the grooves in the back side of the cover plate (described below) in the required operative orientation. The inside face, i.e. the back side, of the cover plate 47, as seen in FIG. 16, is formed with radial channels 55 in which the respective leg portions 56 of the spreader finger elements 39 are reciprocable when positioned therein with the cover plate attached with the inside face turned face to face with the disc-like member 54. The radial channels 55 formed in the inside face of the cover plate 47 and with the leg portions 56 of spreader finger elements 39 positioned therein are, of necessity, open toward the disc-like member 54 so that the guide pins 59 can extend into, and slide along, the spiral guideways 60.

Referring again more particularly to FIGS. 7 and 8, the body portion 41 is seen to encompass the cylindrical bore 44, which is of relatively large diameter compared to the body portion, and extends from the first surface or side 45 to the second surface or side 46 of the body portion. While the assembly apparatus is shown in the drawing figures supported upon a base with the assembly apparatus oriented to receive an end portion of the length of tubing disposed substantially horizontally during the assembly procedure, it is to be understood that the base may be modified, if desired, to support the apparatus with the bore tilted upwardly at any angle to receive the length of tubing, including facing substantially vertically upward, without departing from the scope of the invention. In such event the first or front side of the apparatus as here described would be the upper or top side or surface and the second or back or rear side would be the lower or bottom side or surface of the assembly apparatus.

The first surface 45 of the body portion 41 is substantially covered by the circular cover plate 47 with an aperture 47a located at the center thereof, while the second surface 46 of the body portion 41 is faced with a first retainer ring 52 that has a slightly smaller inner diameter than the diameter of the cylindrical bore 44. The cover plate 47 and the first retainer ring 52 are fastened to the body portion 41, for example, by screws 402, 405, respectively, but it is to be understood that any suitable means of retaining these components in their relative operable positions may be employed.

As best shown in FIGS. 7 and 8, within the cylindrical bore 44, as indicated above, is a rotatable substantially cylindrical sleeve or tube 149, having a first end 50 and a second, smaller, end 51. The rotatable sleeve 149 is retained in the cylindrical bore 44 by a flange or shoulder 53 of the rotatable sleeve which mates with, or fits against, the radially inner portion of the first retainer ring 52 in the vicinity of the second surface 46 of the body portion 41 and a radially outer, forwardly projecting, flange portion 50a of the first end of the rotatable sleeve is retained by the cover plate 47. While the first end portion 50 of the rotatable sleeve 149 has a larger outer diameter than the second end portion 51, hence the flange or shoulder 53, the inside diameter of the cylindrical passageway through the rotatable sleeve is uniform, and the rotatable sleeve will be referred to herein as substantially cylindrical. The second end 51 of the rotatable sleeve 149 is disposed outside of the cylindrical bore 44 and the first retainer ring 52 and is concentrically surrounded by a rotatable control ring 57, preferably of slightly greater diameter than the first retainer ring 52 and preferably having a knurled perimeter surface and/or a lever 61 extending therefrom for easy manipulation. The control ring 57 is bolted or otherwise attached in any suitable manner to the rotatable sleeve 149.

The first end 50 of the rotatable sleeve 149 has a recessed annular end face, having a perimeter flange 50a, as indicated. In the annular recess radially inward from the flange 50a is fitted the disc-like member 54 that is bolted or otherwise fixedly attached to the end face and has a central aperture 54a the same diameter as the central aperture 47a of the cover plate 47, but slightly smaller than the inner diameter of the passageway through the rotatable sleeve 149. The rotatable disc-like member 54 has one face contacting the face of the annular recessed end of the rotatable sleeve 149 to which it is attached and the opposing face is face to face with and rotatable against the inside face of the front cover plate 47, which is attached to the body portion 41 and not rotatable.

Figure 23:
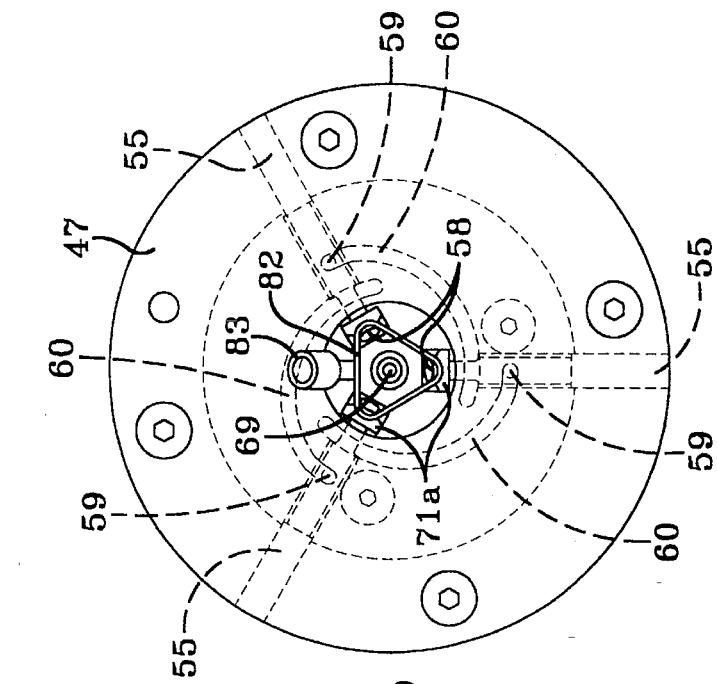
FIG. 23 is a front elevation of the portion of the assembly apparatus encompassed by the cover plate at the point of the assembly process illustrated in FIGS. 21 and 22.

As seen in FIGS. 23 and 25 in dotted outline and in perspective in FIG. 16, the reverse side of the cover plate 47 is provided with three equiangularly-spaced channels 55 which are open sided towards the disc-like member 54 and extend radially outwardly from the central aperture 47a of the cover plate. Inserted reciprocably in each radially extending channel 55 from the central aperture 47a is a leg portion 56 of an "L"-shaped spreader finger element indicated generally by the reference numeral 39. The spreader finger portions 58 extend out of the central aperture 47a of the front cover plate 47 substantially parallel to the axis of the bore 44 to form a cluster and it is this cluster that is manipulated radially apart to spread a tubular segment, such as a tubular segment end portion of a pinch valve element, to permit telescopic assembly thereof upon, i.e., concentrically with, a length of tubing. The spreader finger portions 58, upon which tubular segments are placed for spreading, i.e., stretching to a larger cross-sectional opening, during telescopic assembly of a flexible tubular segment with a length of tubing according to the invention, are preferably quite thin for easier removal of the assembled tubular segment and tubing combination from the assembly apparatus. In this regard it should be noted that the spreader finger portions 58 are sandwiched between a tubular segment end portion 82, 83 of the pinch valve element and the tubing 49 when the spreader finger portions are retracted prior to the ejection step.

In FIGS. 12, 14 and 15, the disc-like member 54 is shown to have formed therein three parallel and radially, i.e. spirally, outward extending spiral guideways 60 which are open-sided towards the cover plate 47. Each spiral guideway extends spirally out in the same direction of rotation from the central aperture 54a of the disc-like member 54. Each leg portion 56 of a respective "L"-shaped spreader finger element 39 is provided with a guide pin 59 fixedly attached thereto that extends laterally from the radial channel 55 of the cover plate 47, in which the leg portion 56 reciprocates, into one of the spiral guideways 60 along which it is slideable. Instead of the spiral guideways shown cut entirely through the disc-like member 54, the guideways 60 may be grooves cut to the same pattern if they are each deep enough to readily receive and slideably guide a guide pin 59 during rotation of the disc-like member 54 and the grooves are open sided towards the cover plate 47.

Upon rotation of the disc-like member 54, using the knurled control ring 57 or the lever 61 to rotate the rotatable sleeve 149 to which the disc-like member 54 is attached, cam-like action is obtained to radially spread or retract the spreader finger portions 58 away from or towards the common axis as the leg portions 56 are moved radially by the respective guide pins 59 sliding in the spiral grooves 60. If desired, the lever 61 may be attached to the control ring 57 as seen in FIGS. 4 and 8 and used to rotate the control ring 57 through a sufficient arc to obtain the desired spreading and retracting of the spreader finger portions 58.

Positioned in the cylindrical passageway of the rotatable sleeve 149 and extending rearwardly therefrom is the reciprocable piston 62 that reciprocates through a short range of movement within the cylindrical passageway of the rotatable sleeve 149 to carry out the very important ejection procedure. The piston 62 is urged resiliently out of the passageway of the rotatable sleeve 149 by the coil spring 63 that bears at one end of the coil spring against the annular portion of the face of the disc-like member 54 that extends radially inward somewhat from the central aperture of the rotatable sleeve 149, and at the other end, against the first end 65 of the piston 62. The rear portion 64 of the second end of the piston 62 is of a slightly smaller diameter than the first portion 65, the rear end of the larger diameter portion constituting a shoulder on the piston, and a second retainer ring 66 attached to the control ring 57 has a central aperture smaller enough than the larger diameter of the first portion 65 of the piston to catch the shoulder and limit the reciprocation of the piston 62 in the rearward direction.

Mounted in a recess in the face of the first end 65 of the piston 62 is an ejector block 68 that is dimensioned longitudinally to serve as a stop to accurately limit the depth of insertion of a length of tubing on which a tubular segment, such as a pinch valve element, is to be emplaced.

Figure 28:
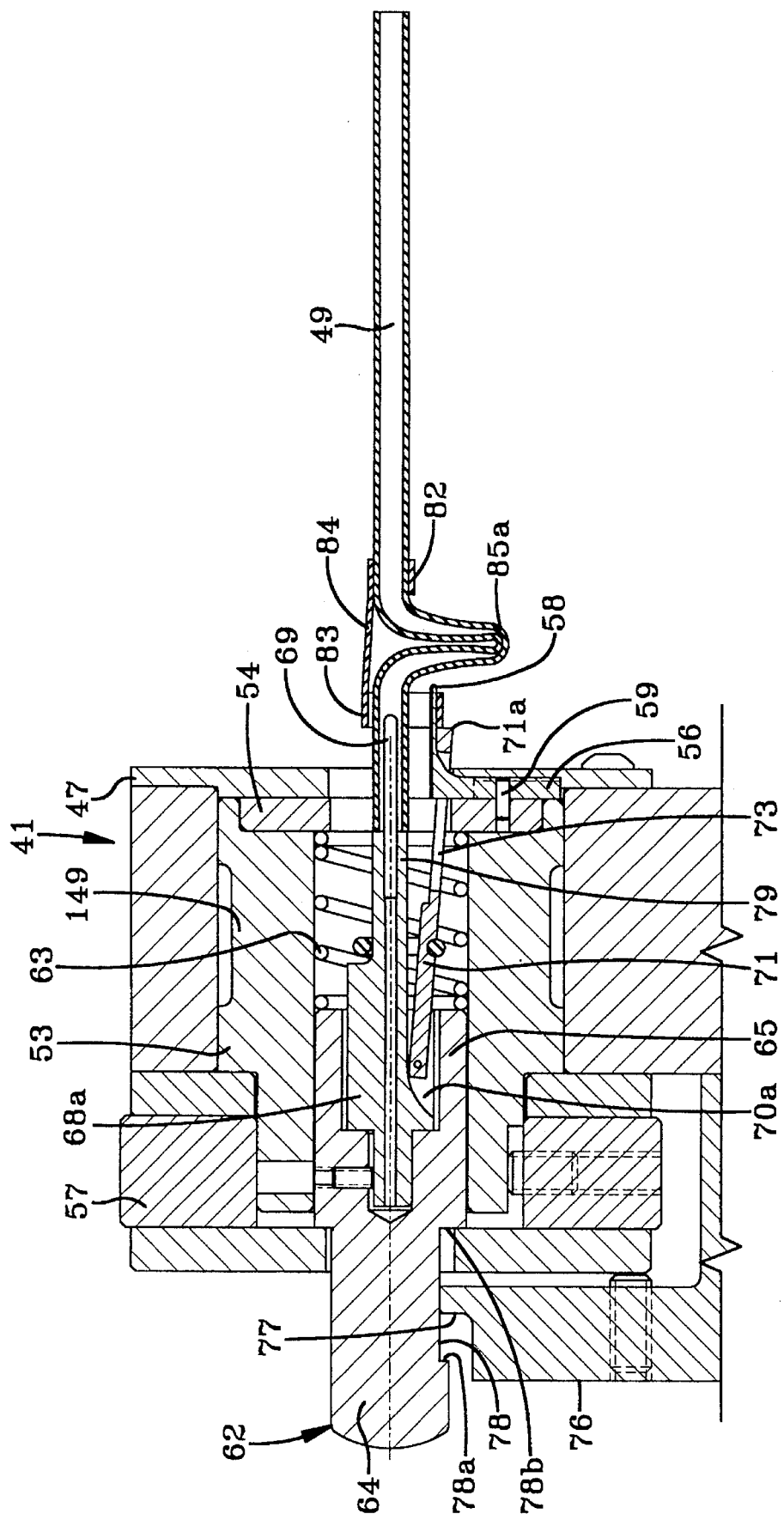
FIG. 28 is a fragmentary view in section of the assembly apparatus and stretched second tubular end portion of the pinch valve element shown in FIG. 27, and with the length of tubing inserted into the apparatus over the central guide rod and through the cluster of spreader fingers.
Figure 29:
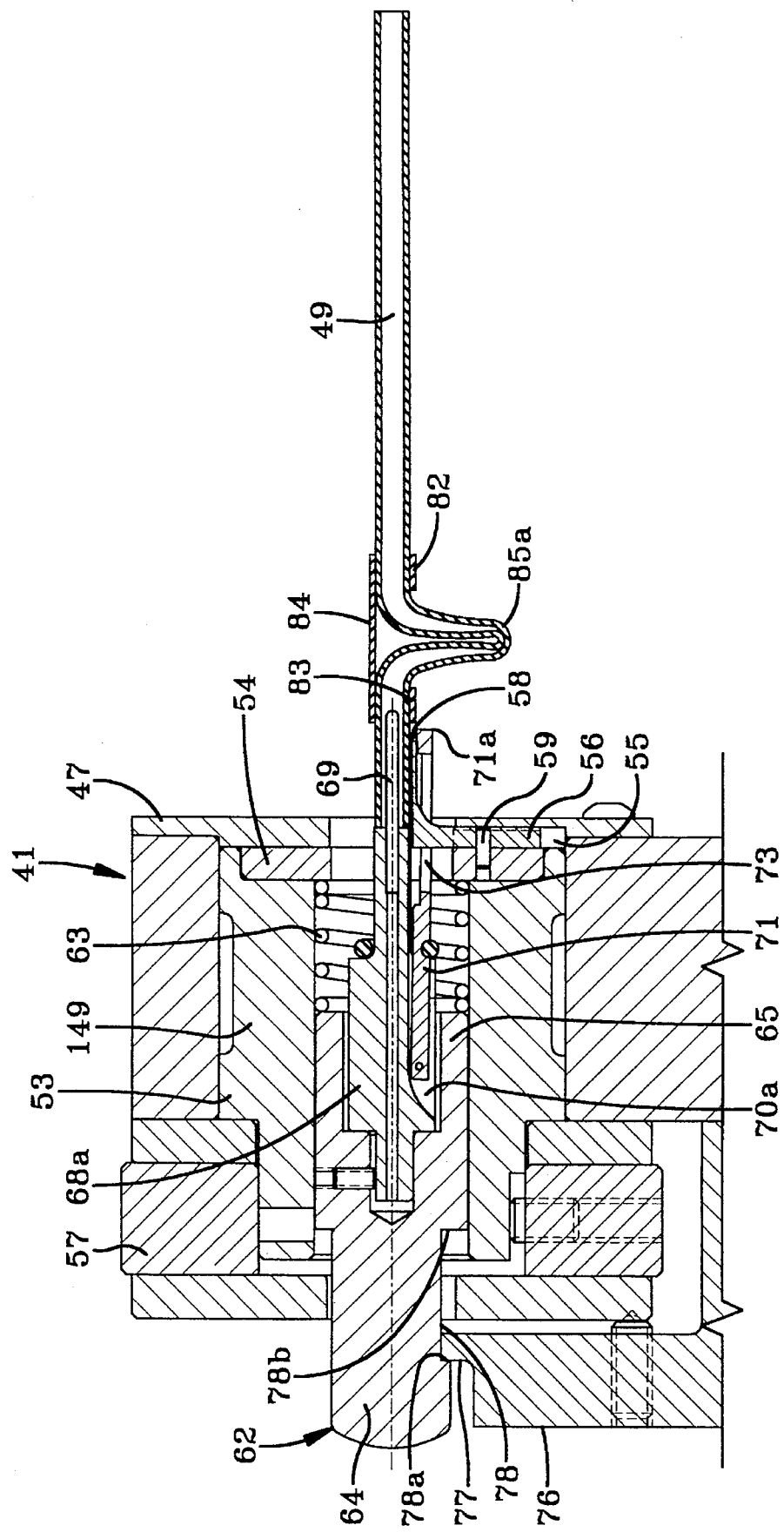
FIG. 29 is a fragmentary view in section of the assembly apparatus with the tubular segment of the pinch valve relaxed upon the length of tubing and the ejector piston moved forward.

In FIGS. 28 and 29 there is shown an assembly apparatus with an ejector block 68a with a longer axial dimension that provides a shallower stop for tubing inserted into the apparatus for the purpose of assembling the second tubular segment end portion of a pinch valve element as a second step in the process of assembling a pinch valve.

A central guide rod 69 extends axially from the ejector block 68 or 68a through the passageway of the rotatable sleeve 149 and substantially to the outward ends of the spreader finger portions 58 where it is centered between them. It serves as a guide over which the length of flexible tubing is inserted into the assembly apparatus. Also pivotably mounted are ejector arms 71 that extend forwardly along inside the passageway of the rotatable sleeve 149 and nearly parallel to the common axis and out through the aperture 54a in the disc-like member 54 and aperture 47a in the cover plate 47 where they each rest against the radially outward surface of a spreader finger portion 58, being collectively resiliently urged against respective spreader fingers by a springy resilient annular member 72, such as an "O" ring. The ejector arms 71 must be selected to be of the appropriate length to contact and bear against the edge of a flexible tubular segment, such as a tubular segment end portion of a pinch valve element, that has just been emplaced on a length of flexible tubing extending into the apparatus, simultaneously with contact and pressure between the ejector block and the inner end of the flexible tubing within the apparatus, in order to avoid moving or displacing the tubular end portion longitudinally of the flexible tubing during ejection. Because of the elastic radially inward tension of the tubular segment end portions of the pinch valve element upon the flexible tubing, which has an outer diameter as great or greater than the inner diameter of the tubular segments, it is not practically feasible to remove the assembled pinch valve from the spreader finger portions without risking altering of the positions of the tubular segment end portions of the pinch valve element, unless use is made of the ejection components of the apparatus.

The second end or part 64 of the reciprocable ejection piston 62 is shown in FIGS. 4 and 7 to be supported by a support element 74 having a lower section 75 thereof attached to the rear of the base portion 42 of the assembly apparatus and an upright leg portion 76 extending upwardly to contact the rear part 64 of the piston which is slideable on the flanged upper end 77 of the leg portion 76. A section 78 of the underside of the rear part 64 of the piston 62 is ground flat from adjacent the second end to the larger diameter forward part 65 of the piston 62, and it is this flat section that rests upon the flanged upper end 77 of the leg portion 76 of the support element 74. The flat nature of the underside section 78 serves to prevent the piston 62 from rotating during use, and the shoulders 78a, 78b formed at each end of the flat section 78 catch, respectively, on the flanged upper end 77 of the support element 74 and on the second retainer ring 66 to provide respective stop actions in the reciprocal motion of the piston 62.

In manufacturing a tension responsive pinch valve of the sort defined herein, it is essential to the proper valving action of the pinch valve that the tubular segment end portions of the pinch valve element be positioned with some accuracy spaced apart a rather short interval longitudinally, i.e., linearly, of the length of tubing, with the magnitude of the interval or spacing being substantially greater than the length of the shank of the pinch valve element. Such larger spacing linearly along the tubing is essential in order to obtain a doubling over of the tubing that produces a pinching shut of the embraced portion of the tubing when there is no tension on the portion of the length of tubing that includes the pinch valve per se and the shank of the pinch valve element tends to elastically assume about its normal length, drawing the attached tubular segment end portions mutually closer. Proper spacing during telescopic assembly is readily achievable in a convenient, efficient way using two nearly identical embodiments of the assembly apparatus described herein differing primarily in having ejector blocks of differing appropriate lengths to assemble the respective tubular segments. The ejector blocks serve as stops in indexing the length, or extent, the end of the length of tubing can extend into the assembly apparatus during the assembly process, thus controlling the positioning of the tubular segment end portions.

The first embodiment of the assembly apparatus utilized will have a relatively short ejector block, such as that identified by the reference numeral 68 in FIGS. 7 and 11 and shown in perspective view in FIG. 9, so that the end of the length of tubing will extend relatively deeper into the assembly apparatus and the first tubular segment end portion of the pinch valve element will be emplaced far enough from the inserted end of the flexible tubing to leave room for the necessary spacing between the first and the second tubular segment end portions. The telescopic assembly of the second tubular segment end portion can only be performed closer to the inserted end of the length of tubing, using the assembly apparatus, than the location of the emplacement of the first tubular segment end portion.

The second embodiment of the assembly apparatus used to telescopically assemble the second tubular segment end portion must have a longer ejector block such as that identified by the reference numeral 68a in FIGS. 28 and 29 and shown in perspective view in FIG. 10, so that the flexible tubing will be stopped at a shallower depth for the assembly of the second pinch valve tubular segment end portion closer to the end of the length of flexible tubing than the first tubular segment end portion. The ejector block 68a may be seen in FIG. 10 to have a smaller diameter extension 38b that serves as the actual stop within the assembly apparatus for the end of the length of tubing inserted during assembly operations. The extension 38b has a smaller diameter than the ejector block 68a in order to leave circumferential annular space within the rotatable sleeve 149 for the coil spring 63.

The base, body portion, and parts such as the cylindrical sleeve, reciprocable piston, control ring and both retainer rings, cover plate and disc-like member, of the assembly apparatus may be made of mild steel or of an easily machinable metal, such as aluminum alloy, if desired, but are preferably made of tool steel or stainless steel. Preferably the spreader fingers and the ejector arms are made of tool steel or stainless steel to provide greater strength and durability in the thinner members.

Figure 17:
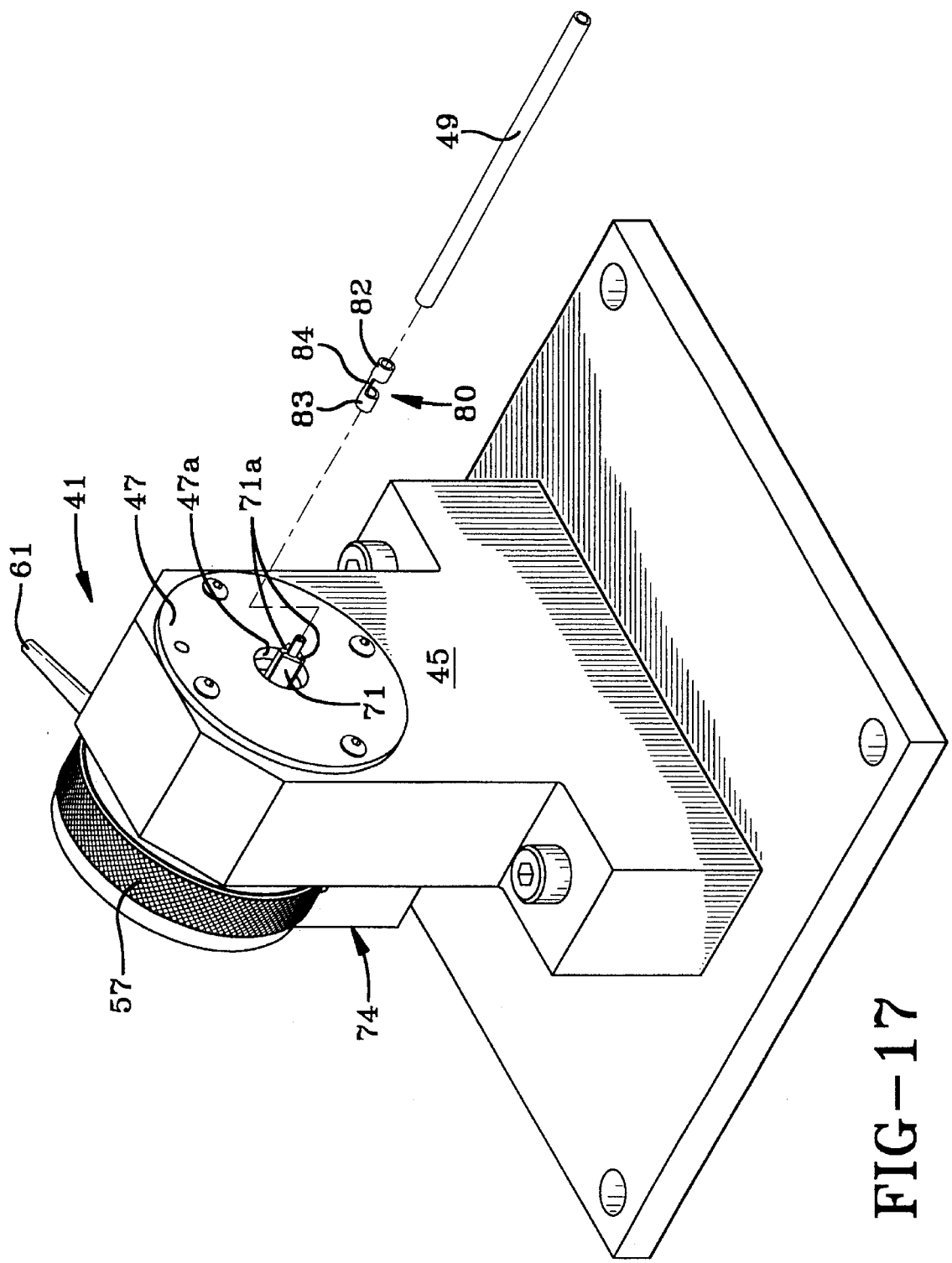
FIG. 17 is a perspective view of the present assembly apparatus with the components of a punch valve shown in exploded view relationship about to be assembled using the assembly apparatus.

Referring now to FIG. 17 there is depicted an embodiment of the assembly apparatus, along with a flexible pinch valve element 80 and a length 49 of flexible tubing of the same diameter depicted in exploded view. The pinch valve element 80, which consists of first 82 and second 83 foreshortened tubular segments as end portions joined by a short shank portion 84 of about the same length as the end portions, is about to be telescopically assembled on the length 49 of flexible tubing near an end thereof. The embodiment of the assembly apparatus shown in FIG. 17 its to be understood to be equipped with an ejector block 68 of appropriate length for positioning the first tubular segment 82 of the pinch valve element 80.

Figure 18:
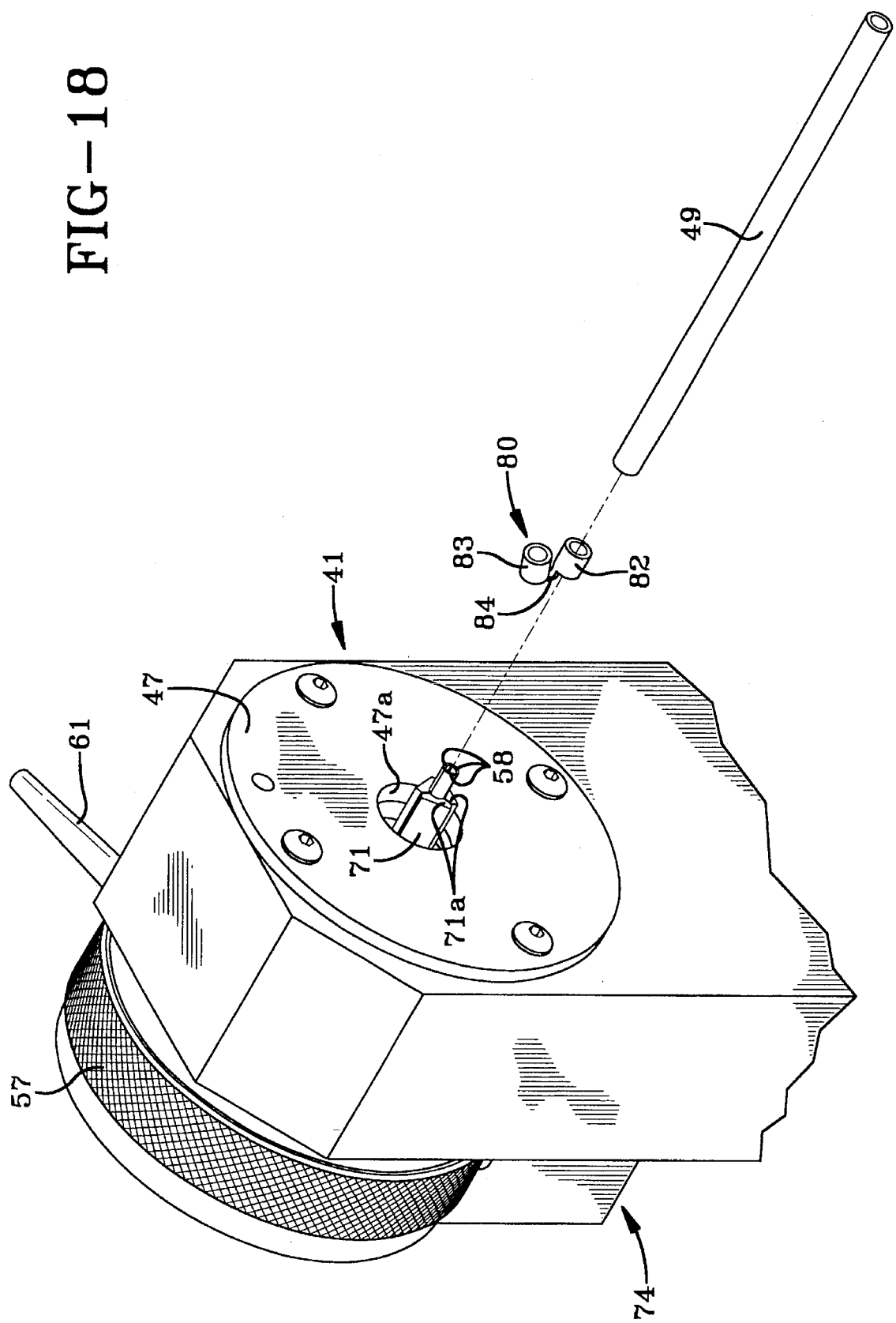
FIG. 18 is a fragmentary perspective view of the assembly apparatus shown with a tubular end portion of the pinch valve element oriented for placing over, i.e., around, the fingers of the spreader finger elements.
Figure 19:
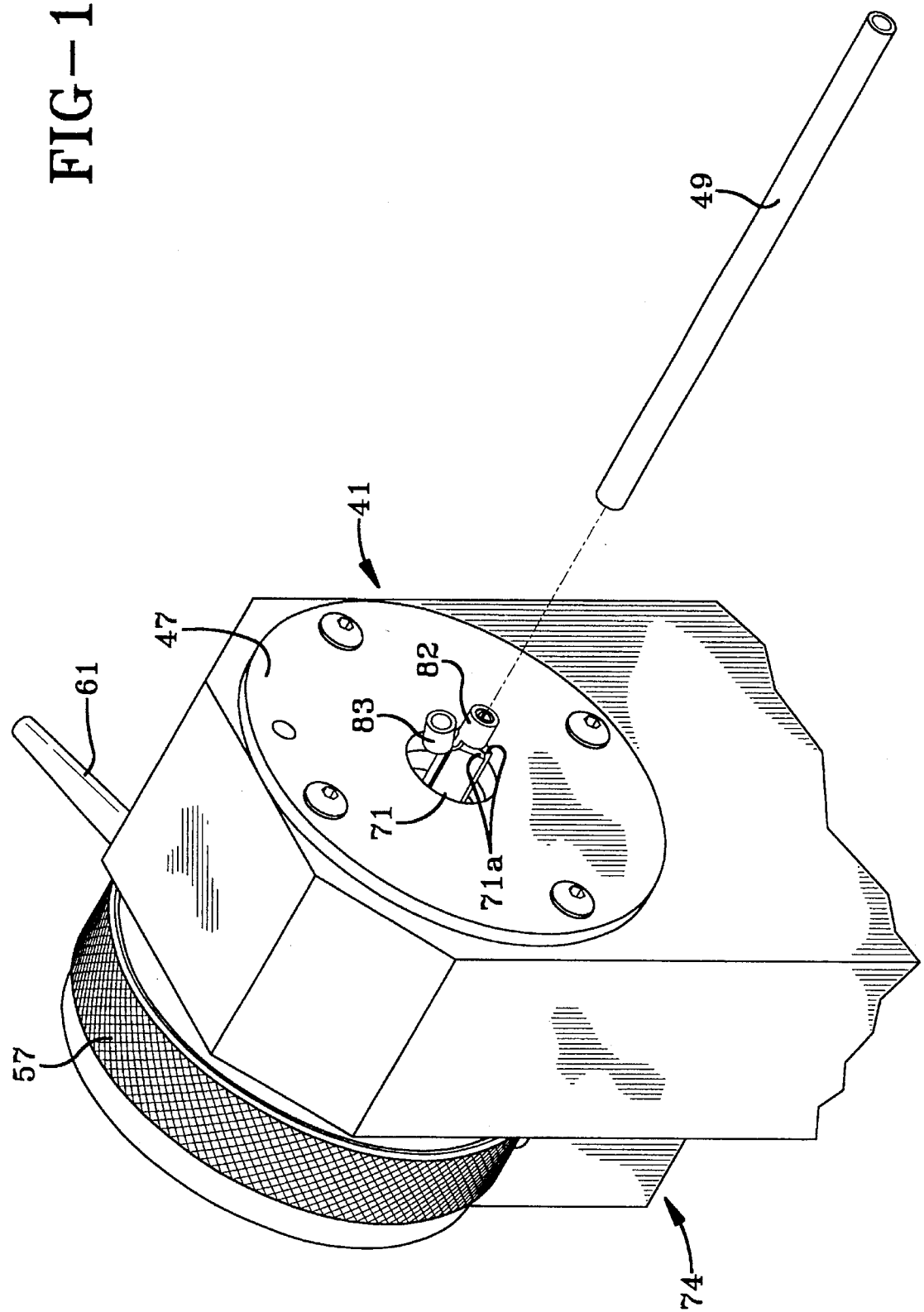
FIG. 19 is a view similar to FIG. 18 with a tubular end portion of the pinch valve element slid onto the cluster of spreader fingers to commence the assembly process.
Figure 20:
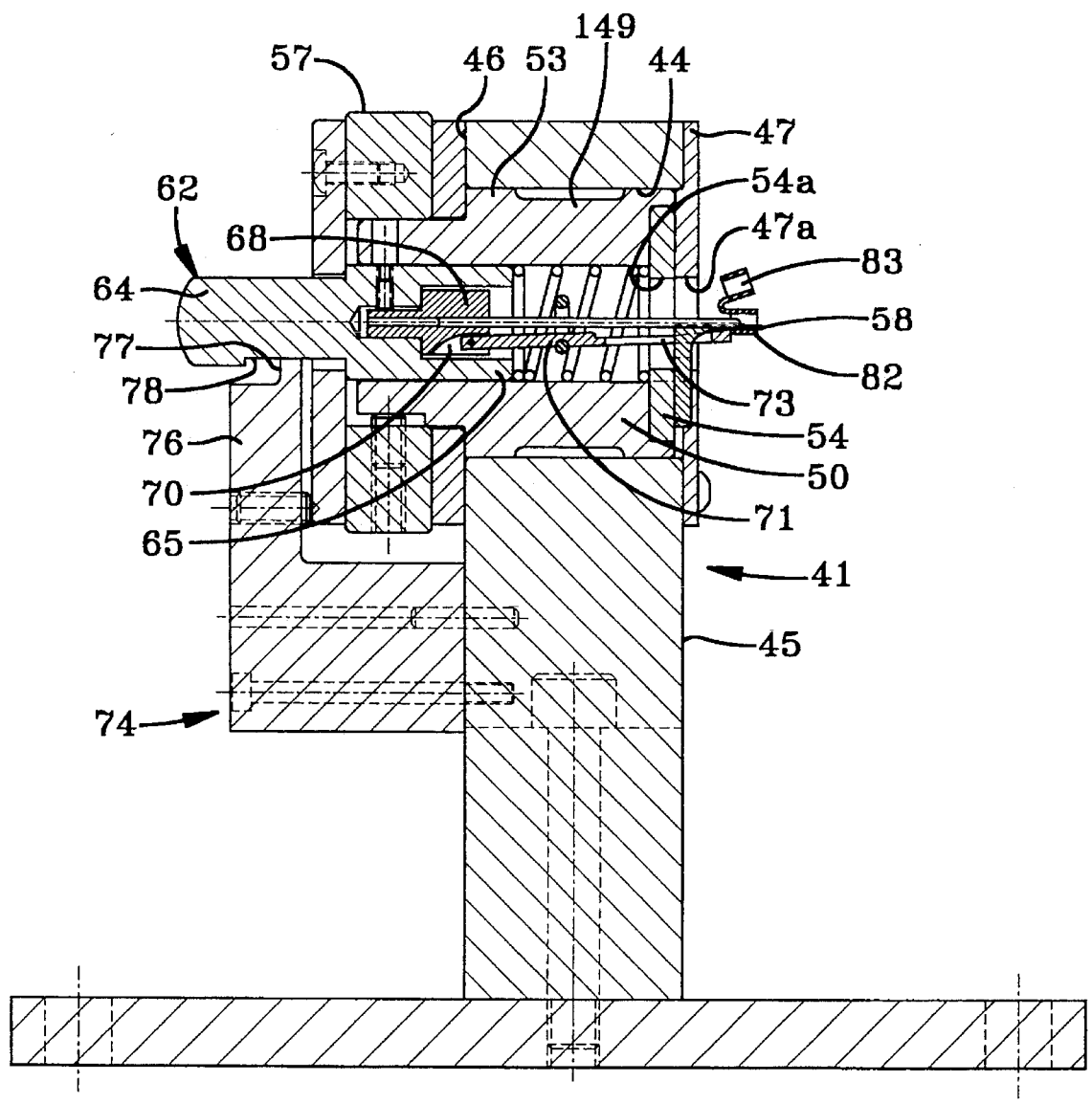
FIG. 20 is a view in vertical section of the present assembly apparatus like that shown in FIG. 7, but with a tubular segment, namely a tubular end portion of the pinch valve element, emplaced over the spreader fingers as in FIG. 19.

The pinch valve element 80 is seen in FIG. 18 to be poised for assembly on the length 49 of flexible tubing with the shank portion 84 of the pinch valve element bent aside to hold the second tubular segment end portion 83 out of the way so the first tubular segment end portion 82 can be slipped over the spreader finger portions 58 that are retracted close together as a cluster as depicted in FIG. 18. In FIG. 19 the tubular segment end portion 82 is shown slipped onto the cluster of spreader finger portions 58. The inner edge of the first tubular segment end portion should be in contact with the ends 37a of the ejector arms 31 to ensure accurate positioning during the assembly process. The section view in FIG. 20 also shows the tubular segment end portion 82 slipped onto the spreader finger portions 58. In FIG. 20 it is also seen that the apparatus is equipped with a fairly short ejector block 68 inside the first end 65 of the ejector piston 62.

Rotation of the control ring 57, which concentrically surrounds and is attached to the rear end of the larger diameter portion of the rotatable sleeve 149, causes rotation of the rotatable sleeve as well as the disc-like member 54 which is mounted on the front end 50 of the rotatable sleeve. Rotation of the disc-like member 54 forces the guide pins 59 attached to respective leg portions 56 of spreader finger elements 39 to slide along the spiral guideways 60 of the disc-like member, giving cam-like action moving the leg portions 56 in a radial direction within the radial channels in the cover plate 47 and the spreader finger portions 58 of the spreader finger elements 39 are consequently moved radially as well, which is the desired action. The direction and extent of rotation of the disc-like member 54 determines the radial direction and extent of movement of the spreader finger portions 58.

Figure 21:
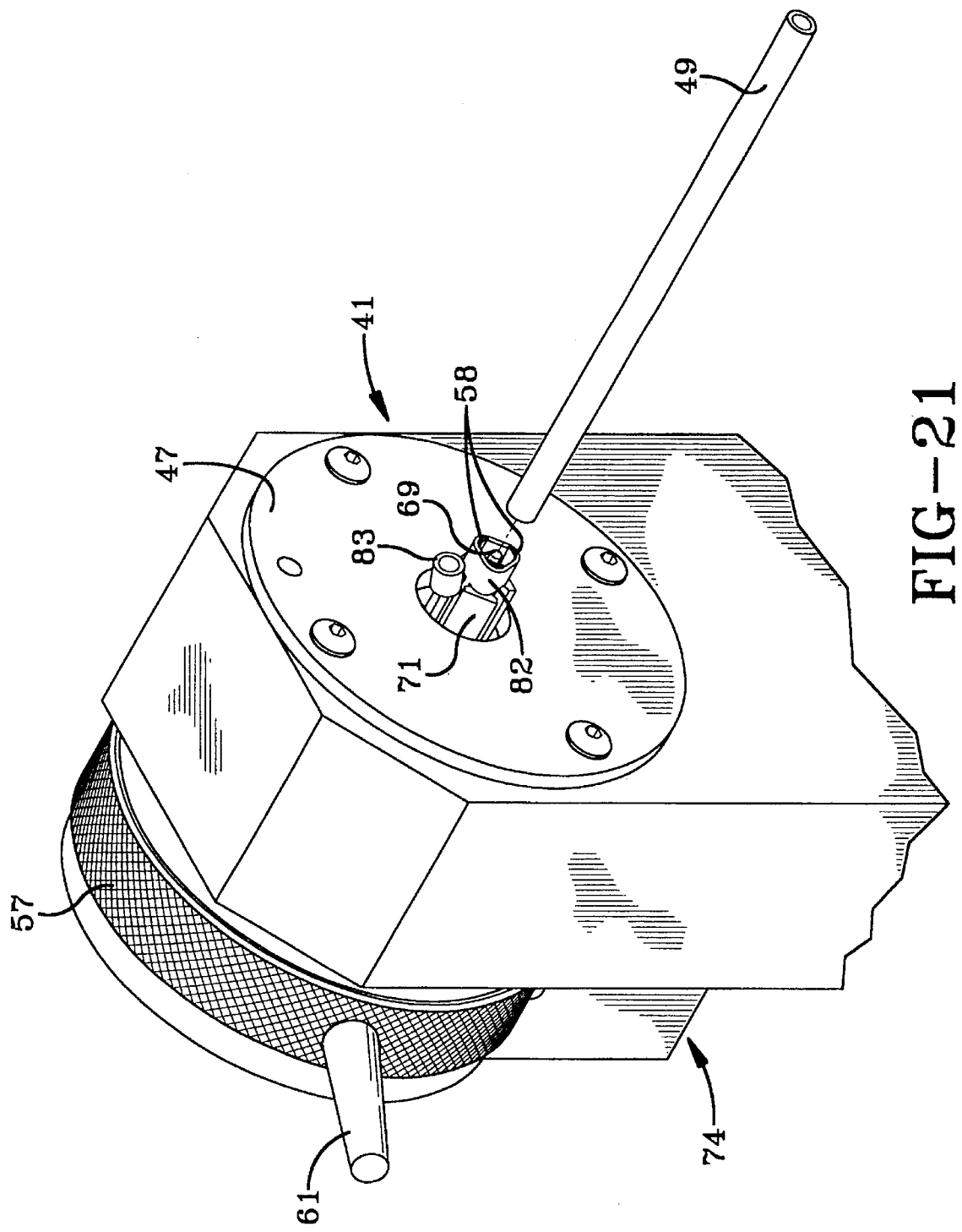
FIG. 21 is a perspective fragmentary view similar to FIG. 19 showing the tubular end portion of the pinch valve element shown in FIG. 19 stretched open radially to receive therethrough the length of tubing upon which the valve element is to be telescopically assembled.
Figure 22:
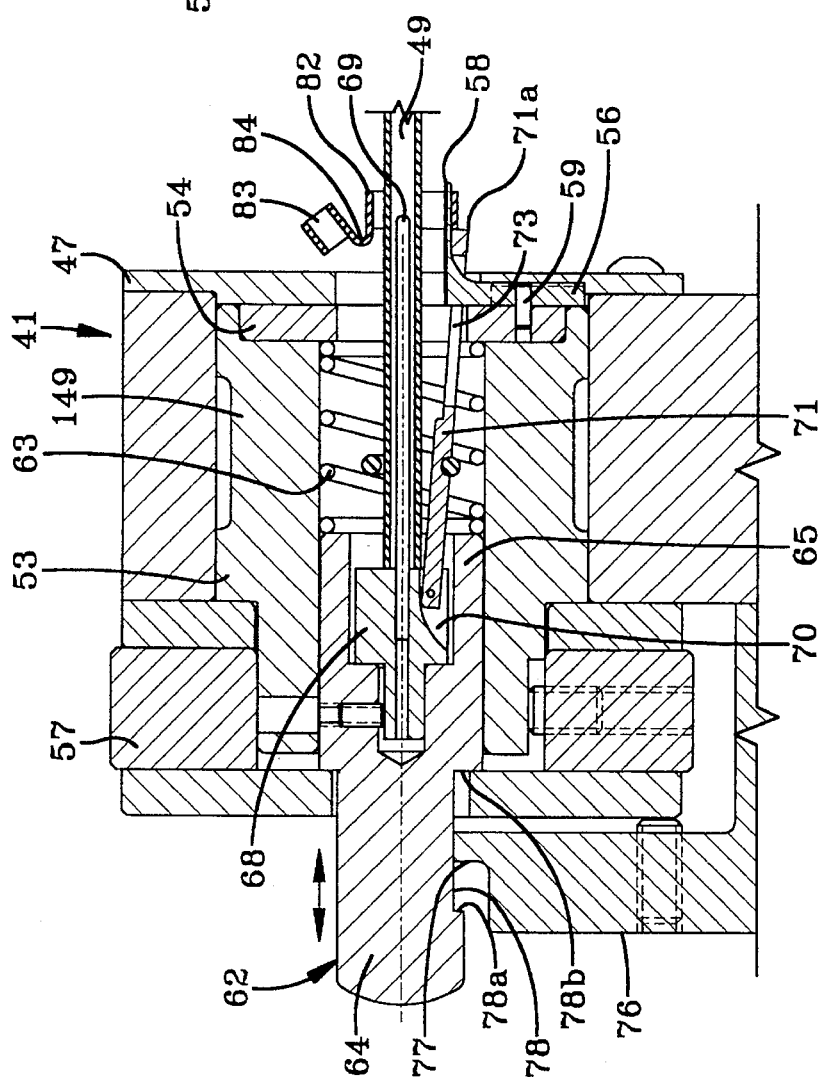
FIG. 22 is a fragmentary view in section of the assembly apparatus and stretched tubular end portion of the pinch valve element shown in FIG. 21, and with the length of tubing inserted into the apparatus over the central guide rod and through the cluster of spreader fingers.

In the next assembly step the control ring 57 is then grasped and rotated manually, or the lever 61 may be used to rotate the control ring 57, in the appropriate direction and through an arc sufficient to spread the spreader finger portions 58, thus stretching the first tubular segment end portion 82 open as shown in FIGS. 21, 22 and 23. Turning the control ring 57 sufficiently stretches the tubular segment 82 enough to admit the end of the length of tubing 49 which is then slid through the tubular segment with little or no friction and onto central guide rod 69 until the end of the length of tubing hits the ejector block 68, which serves as a stop for the proper positioning of the tubular segment end portion 82 on the length of tubing 49. The control ring 57 is then rotated as by moving the lever 61 back towards its starting position to relax the spreading tension on the first tubular segment end portion 82, completing the assembly step for the first tubular segment end portion.

To carry out ejection, the ejector piston 62 is moved forward (towards the first surface 45 of the body portion 41) by any suitable means against the coil spring 63 to move the ejector piston a small distance or spacing from a position with the second or rear end 64 extending back beyond the support element 74 until the ejector piston 62 reaches a preset stop as seen in FIG. 24 where the rear edge 78a of the flattened lower surface 78 of the rear part 64 of the piston is caught by the upstanding flanged upper end 77 of the upright leg section 76 of support element 74. The piston 62 carries forward the ejector block 68 and the ejector arms 71 which contact and eject simultaneously and respectively the end of the length of tubing 49, and the nearest edge of the emplaced tubular segment 82 which is contacted by the ends of the ejector arms 71a, as can be seen in FIGS. 24 and 25. At the pre-set stop the ejector arms 71 and the ejector block 68 will have coordinately mechanically ejected with simultaneous pressure the length 49 of flexible tubing and the emplaced first tubular end portion 82 of the pinch valve element.

While the piston 62 is readily slid forward manually towards the cover plate 47 if the coil spring 63 is selected to be of a suitable spring tension, the piston 62 may be equipped to be reciprocated hydraulically or electromagnetically, if desired.

Figure 26:
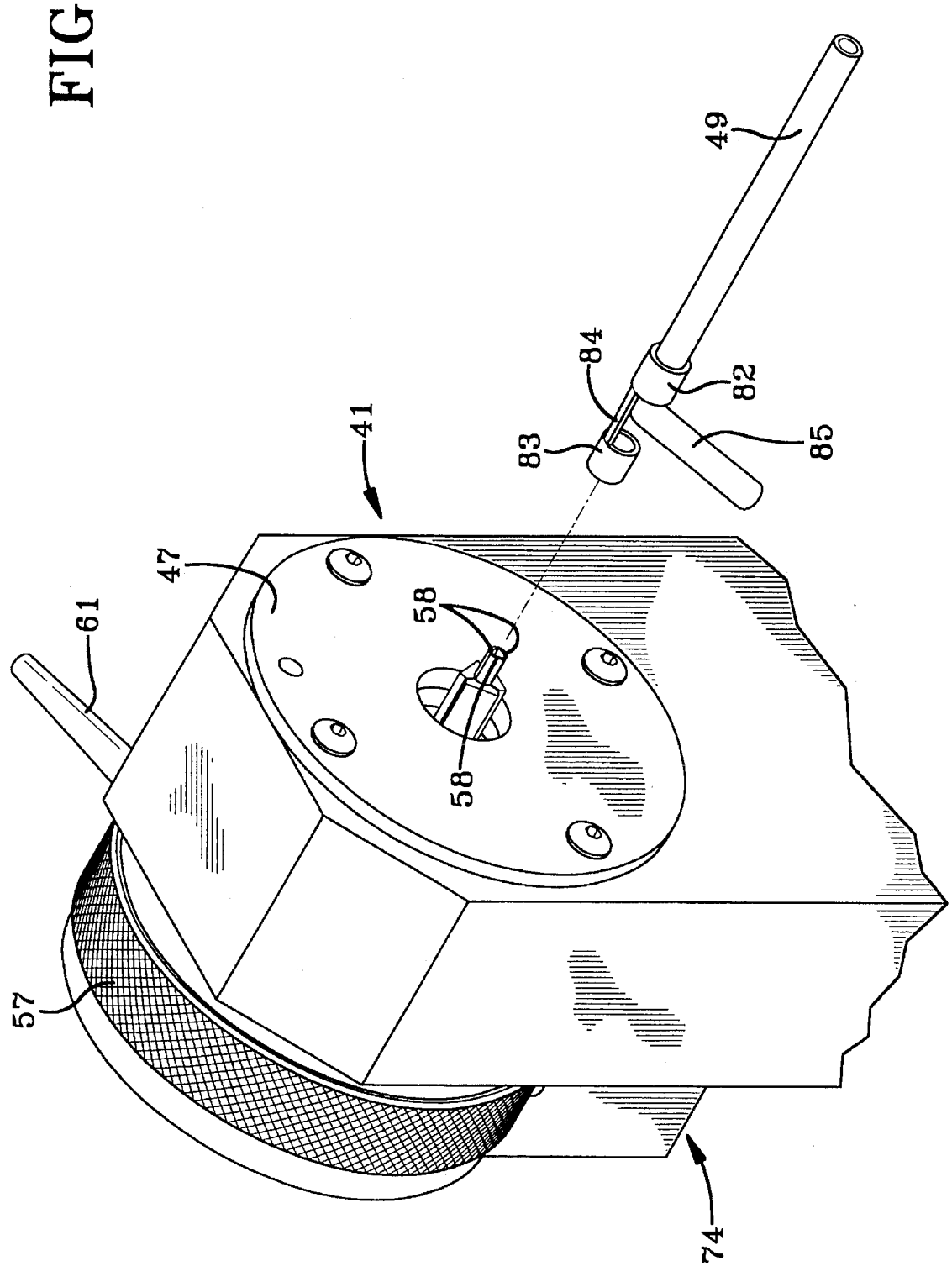
FIG. 26 is a fragmentary perspective view of assembly apparatus closely similar to that of FIG. 18 but adapted with a longer ejector block for the next stage of assembling a pinch valve assembly with the second tubular end portion of the pinch valve element oriented for placing over, i.e., around, the spreader fingers and with the leading end of the length of tubing bent aside temporarily.

In FIG. 26 the partly assembled pinch valve depicted in FIG. 24 is shown poised to be further assembled using a second embodiment of the assembly apparatus with a different, i.e., shallower depth stop, in the form of a longer ejector block 68a with an extension 38b. The short end section 85 of the length 49 of flexible tubing between the leading end thereof and the emplaced first tubular segment end portion 82 of the pinch valve element 80 has been bent out of the way so as not to impede sliding the second tubular segment end portion 83 onto the retracted spreader finger portions 58 of the assembly apparatus until the tubular segment end portion contacts the ends of the ejector arms 71a, the shank portion 84 of the pinch valve element 80 being much shorter than the section of tubing 85a disposed between the tubular segment end portions 82 and 83 which are assembled therewith (i.e. emplaced thereon).

Figure 27:
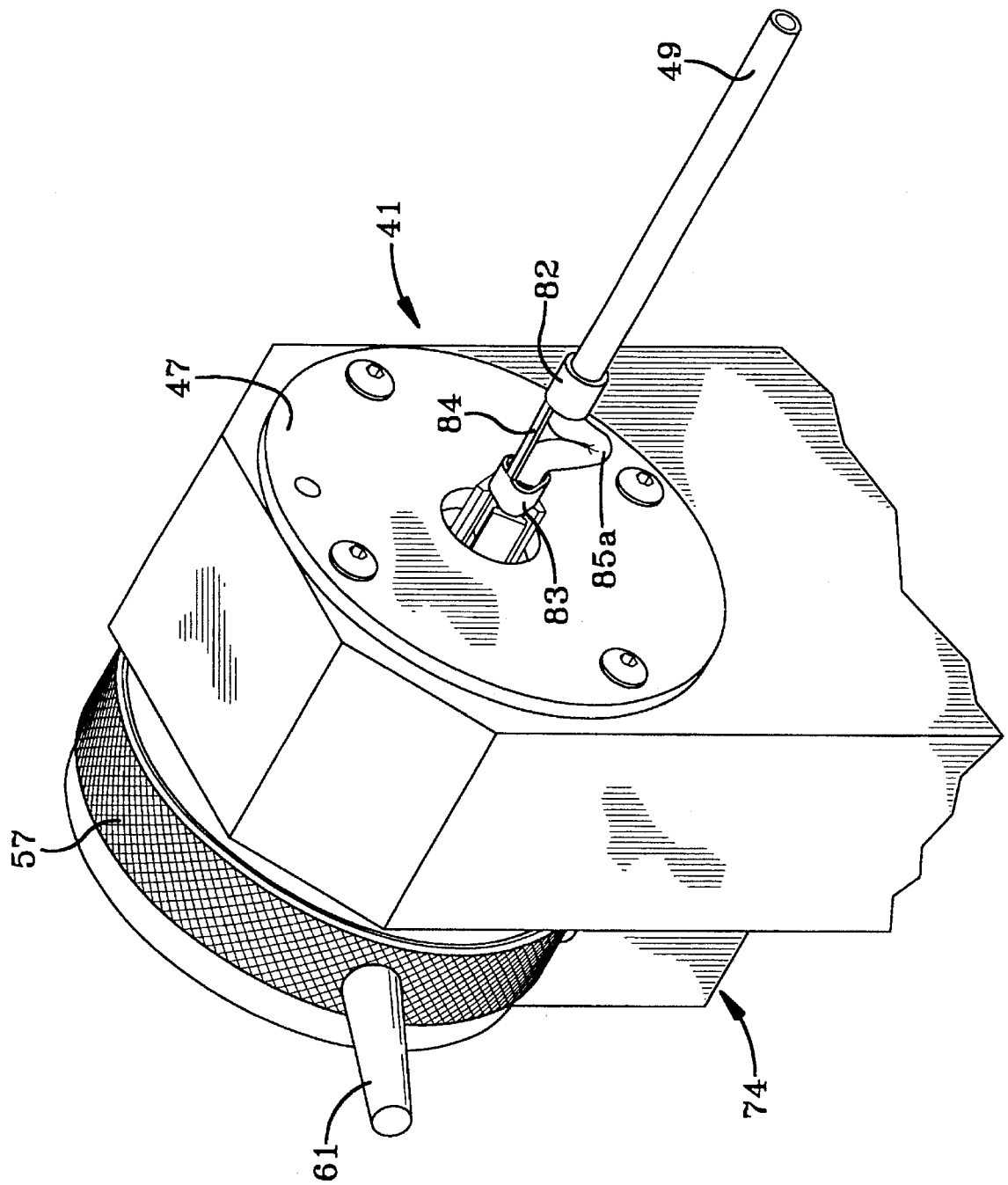
FIG. 27 is a view similar to FIG. 26 showing a further step in the next stage of manufacturing a pinch valve assembly wherein the second tubular end portion is being emplaced on the length of tubing.

The second tubular segment end portion 83 of the pinch valve element is then slid onto the spreader finger portions 58 and the control ring 57 is rotated to spread the spreader finger portions 58 and stretch the second tubular segment end portion 83 of the pinch valve element 80, similar to what is seen in FIG. 21, and the short end section 85 of the length 49 of flexible tubing is bent over sharply and the leading end is slipped inside the spreader finger portions 58 and the stretched second tubular segment end portion 83 and over the central guide rod 69 and up against the ejector block 68a as shown in FIGS. 27 and 28.

As indicated, the longer ejector block 68a, having an extension 38b, provides a stop at a shallower depth of penetration by the end of the length of tubing 49 inside the apparatus. The ejector block 68a is selected to have an extension 38b of appropriate length to provide indexing at a selected depth of penetration desired for the end of the length of tubing 49 in order to achieve proper placement of the second tubular segment end portion 83.

To complete the assembly of the second tubular segment end portion 83 of the pinch valve element, the control ring 57 is rotated back to retract the spreader finger portions 58 closer together to relieve the tension on the second tubular segment end portion 83. To carry out ejection substantially in the same manner as described for the first emplaced tubular segment end portion 82, the ejection piston 62 is pressed forward against the action of the coil spring 63 until the rear edge 78a of the flat lower surface 78 of the rear portion 64 of the ejection piston 62 is stopped by the flanged upper end 77 of the upright leg portion 76 of support element 74, whereupon the length 49 of flexible tubing and the second tubular segment end portion 83 of the pinch valve element emplaced thereon will be found to have been ejected as a unit and the manufacture of the flexible pinch valve is completed.

It is preferred to complete the manufacture of the pinch valve by inserting a small amount of an adhesive such as a room temperature vulcanizing silicone adhesive along the margins of the tubular segment end portions of the valve element.

It will be readily understood that assembly of a single tubular segment with a plug or cap attached by a tether with a length of tubing near an end of the tubing can be carried out in a manner very similar to the procedure set forth above for the assembly of the first tubular segment of the pinch valve element with the tubular segment and cap and tether being properly oriented so that the tether extends toward the end of the tubing to be closed by the cap.

We claim:

1. A method of assembling telescopically a flexible pinch valve element with a length of flexible tubing to form a flexible, tension responsive, pinch valve comprising the steps of:

providing a pinch valve element having a first tubular segment end portion and a second tubular segment end portion joined by a shank portion, said first and second tubular segment end portions having a diameter;

providing a length of flexible tubing having an outer diameter substantially the same as or greater than the diameter of the tubular segment end portions;

providing a first assembly apparatus including: means for controllably radially stretching one of the tubular segment end portions of the pinch valve element during insertion of the flexible tubing into said one of the tubular segment end portions and controllably allowing said one of the tubular segment end portions to radially relax thereafter; means for limiting the depth of insertion of the flexible tubing into the pinch valve element to a first preselected depth; and means for ejecting, from the means for radial stretching and relaxing, the pinch valve element and the flexible tubing that have been telescopically assembled together;

radially stretching the first tubular segment end portion using said means therefor;

inserting the flexible tubing into the stretched first tubular segment end portion to the first preselected depth;

allowing the stretched first tubular segment end portion to relax around the flexible tubing;

simultaneously ejecting from said first assembly apparatus the first tubular segment end portion and the flexible tubing that have been assembled together;

radially stretching the second tubular segment end portion;

inserting the flexible tubing into the stretched second tubular segment end portion; and allowing the stretched second tubular segment end portion to relax around the flexible tubing.

2. A method in accordance with claim 1, wherein said method further comprises the step of:

providing a second assembly apparatus including: means for controllably radially stretching one of the tubular segment end portions of the pinch valve element during insertion of the flexible tubing into said one of the tubular segment end portions and controllably allowing said one of the tubular segment end portions to radially relax thereafter; means for limiting the depth of insertion of the flexible tubing into the pinch valve element to a second preselected depth, said second preselected depth being less than the first preselected depth by a differential length greater than a length of the shank portion of the pinch valve element; and means for ejecting, from the means for radial stretching and relaxing, the pinch valve element and the flexible tubing that have been telescopically assembled together, wherein said second assembly apparatus is used to radially stretch the second tubular segment end portion.

3. A method for assembling a flexible pinch valve element and a length of flexible tubing comprising the steps of:

providing a pinch valve element having a first tubular segment end portion and a second tubular segment end portion joined by a shank portion, said first and second tubular segment end portions having a diameter;

providing a length of flexible tubing having an outer diameter substantially the same as or greater than the diameter of the tubular segment end portions;

radially stretching the first tubular segment end portion;

inserting the flexible tubing into the stretched first tubular segment end portion to a first preselected depth;

allowing the stretched first tubular segment end portion to relax around the flexible tubing;

radially stretching the second tubular segment end portion;

inserting the flexible tubing into the stretched second tubular segment end portion; and allowing the stretched second tubular segment end portion to relax around the flexible tubing.

* * * * *